US008298801B2

(12) United States Patent
Kink et al.

(10) Patent No.: US 8,298,801 B2
(45) Date of Patent: Oct. 30, 2012

(54) METHODS AND COMPOSITIONS FOR THE TREATMENT OF CANCER

(75) Inventors: John A. Kink, Madison, WI (US); Laura E. Strong, Stoughton, WI (US); Mark N. Shahan, Madison, WI (US)

(73) Assignee: Quintessence Biosciences, Inc., Madison, WI (US)

( * ) Notice: Subject to any disclaimer, the term of this patent is extended or adjusted under 35 U.S.C. 154(b) by 0 days.

(21) Appl. No.: 11/879,279

(22) Filed: Jul. 17, 2007

(65) Prior Publication Data
US 2008/0095755 A1    Apr. 24, 2008

Related U.S. Application Data

(60) Provisional application No. 60/831,378, filed on Jul. 17, 2006.

(51) Int. Cl.
*C12N 9/22* (2006.01)
*C12N 9/14* (2006.01)
*C12N 9/16* (2006.01)
*C12N 9/00* (2006.01)
*A61K 38/46* (2006.01)
*A61K 38/47* (2006.01)

(52) U.S. Cl. ........ 435/199; 435/183; 435/195; 435/196; 424/94.6; 424/94.61

(58) Field of Classification Search .................. None
See application file for complete search history.

(56) References Cited

U.S. PATENT DOCUMENTS

| | | | |
|---|---|---|---|
| 4,424,311 A | 1/1984 | Nagaoka |
| 4,708,930 A | 11/1987 | Kortright |
| 4,743,543 A | 5/1988 | Kortright |
| 4,892,935 A | 1/1990 | Yoshida |
| 4,914,021 A | 4/1990 | Toth |
| 4,918,164 A | 4/1990 | Hellstrom |
| 4,921,789 A | 5/1990 | Salem |
| 4,921,790 A | 5/1990 | O'brien |
| 4,939,240 A | 7/1990 | Chu |
| 4,963,484 A | 10/1990 | Kufe |
| 5,053,489 A | 10/1991 | Kufe |
| 5,096,815 A | 3/1992 | Ladner et al. |
| 5,110,911 A | 5/1992 | Samuel |
| 5,198,346 A | 3/1993 | Ladner et al. |
| 5,200,182 A | 4/1993 | Kiczka |
| 5,223,409 A | 6/1993 | Ladner et al. |

(Continued)

FOREIGN PATENT DOCUMENTS

EP    1316318    6/2003
(Continued)

OTHER PUBLICATIONS

Leland, P.A., et al. "Endowing Human Pancreatic Ribonuclease with Toxicity for Cancer Cells" J. Biol. Chem. 2001, 276 (46), pp. 43095-43102.*

(Continued)

*Primary Examiner* — Chris R Tate
*Assistant Examiner* — Aaron J Kosar
(74) *Attorney, Agent, or Firm* — Casimir Jones, S.C.

(57) ABSTRACT

The present invention is directed toward the delivery of toxic agents to pathogenic cells, particularly cancer cells. In some embodiments, the toxic agent is a human ribonuclease or similar agent that is toxic to cells.

9 Claims, 23 Drawing Sheets

U.S. PATENT DOCUMENTS

| | | |
|---|---|---|
| 5,270,163 A | 12/1993 | Gold |
| 5,270,204 A | 12/1993 | Vallee et al. |
| 5,286,487 A | 2/1994 | Vallee et al. |
| 5,286,637 A | 2/1994 | Veronese et al. |
| 5,359,030 A | 10/1994 | Ekwuribe |
| 5,389,537 A | 2/1995 | Raines et al. |
| 5,446,090 A | 8/1995 | Harris |
| 5,475,096 A | 12/1995 | Gold |
| 5,512,443 A | 4/1996 | Schlom |
| 5,545,530 A | 8/1996 | Satomura |
| 5,559,212 A | 9/1996 | Ardelt |
| 5,562,907 A | 10/1996 | Arnon |
| 5,660,827 A | 8/1997 | Thorpe et al. |
| 5,672,662 A | 9/1997 | Harris |
| 5,693,763 A | 12/1997 | Codington |
| 5,733,731 A | 3/1998 | Schatz et al. |
| 5,739,208 A | 4/1998 | Harris |
| 5,786,457 A | 7/1998 | Nett et al. |
| 5,808,005 A | 9/1998 | Codington |
| 5,811,238 A | 9/1998 | Stemmer et al. |
| 5,824,544 A | 10/1998 | Armentano et al. |
| 5,824,784 A | 10/1998 | Kinstler |
| 5,830,721 A | 11/1998 | Stemmer et al. |
| 5,830,730 A | 11/1998 | German et al. |
| 5,837,458 A | 11/1998 | Minshull et al. |
| 5,840,296 A | 11/1998 | Raines et al. |
| 5,840,840 A | 11/1998 | Rybak et al. |
| 5,855,866 A | 1/1999 | Thorpe |
| 5,866,119 A | 2/1999 | Bandman et al. |
| 5,872,154 A | 2/1999 | Wilson et al. |
| 5,885,808 A | 3/1999 | Spooner et al. |
| 5,892,019 A | 4/1999 | Schlom |
| 5,892,020 A | 4/1999 | Mezes |
| 5,900,461 A | 5/1999 | Harris |
| 5,932,462 A | 8/1999 | Harris |
| 5,955,073 A * | 9/1999 | Rybak et al. ............... 424/94.61 |
| 5,981,225 A | 11/1999 | Kochanek et al. |
| 5,990,237 A | 11/1999 | Bentley |
| 5,994,106 A | 11/1999 | Kovesdi et al. |
| 5,994,128 A | 11/1999 | Fallaux et al. |
| 5,994,132 A | 11/1999 | Chamberlain et al. |
| 6,001,557 A | 12/1999 | Wilson et al. |
| 6,019,978 A | 2/2000 | Ertl et al. |
| 6,033,908 A | 3/2000 | Bout et al. |
| 6,045,793 A | 4/2000 | Rybak et al. |
| 6,051,230 A | 4/2000 | Thorpe et al. |
| 6,077,499 A | 6/2000 | Griffiths et al. |
| 6,083,477 A | 7/2000 | Goldenberg |
| 6,183,744 B1 | 2/2001 | Goldenberg |
| 6,197,528 B1 | 3/2001 | Wu et al. |
| 6,214,966 B1 | 4/2001 | Harris |
| 6,271,369 B1 | 8/2001 | Torrence et al. |
| 6,280,991 B1 | 8/2001 | Raines |
| 6,312,694 B1 | 11/2001 | Thorpe et al. |
| 6,348,558 B1 | 2/2002 | Harris |
| 6,362,254 B2 | 3/2002 | Harris |
| 6,362,276 B1 | 3/2002 | Harris |
| 6,395,276 B1 | 5/2002 | Rybak et al. |
| 6,399,068 B1 | 6/2002 | Goldenberg |
| 6,406,897 B1 | 6/2002 | Kim et al. |
| 6,416,758 B1 | 7/2002 | Thorpe et al. |
| 6,432,397 B1 | 8/2002 | Harris |
| 6,437,025 B1 | 8/2002 | Harris |
| 6,448,369 B1 | 9/2002 | Bentley |
| 6,515,100 B2 | 2/2003 | Harris |
| 6,541,543 B2 | 4/2003 | Harris |
| 6,541,619 B1 | 4/2003 | Park et al. |
| 6,610,281 B2 | 8/2003 | Harris |
| 6,649,383 B1 | 11/2003 | Cheung |
| 6,649,393 B1 | 11/2003 | Youle et al. |
| 6,653,104 B2 | 11/2003 | Goldenberg |
| 6,664,331 B2 | 12/2003 | Harris |
| 6,737,505 B2 | 5/2004 | Bentley |
| 6,828,401 B2 | 12/2004 | Nho |
| 6,838,076 B2 | 1/2005 | Patton |
| 6,864,327 B2 | 3/2005 | Bentley |
| 6,864,350 B2 | 3/2005 | Harris |
| 6,894,025 B2 | 5/2005 | Harris |
| 7,199,223 B2 | 4/2007 | Bossard |
| 7,355,019 B2 | 4/2008 | Backer et al. |
| 7,416,875 B2 | 8/2008 | Raines et al. |
| 7,476,725 B2 | 1/2009 | Zalipsky |
| 2001/0049434 A1 | 12/2001 | Conklin et al. |
| 2002/0006379 A1 | 1/2002 | Hansen et al. |
| 2002/0037289 A1 | 3/2002 | Thorpe et al. |
| 2002/0048550 A1 | 4/2002 | Vallera et al. |
| 2002/0106359 A1 | 8/2002 | Gokcen |
| 2002/0119153 A1 | 8/2002 | Thorpe et al. |
| 2002/0187153 A1 | 12/2002 | Goldenberg |
| 2003/0031669 A1 | 2/2003 | Goldenberg |
| 2003/0114368 A1 | 6/2003 | Rybak |
| 2003/0219785 A1 | 11/2003 | Hallahan et al. |
| 2005/0158273 A1 | 7/2005 | Harris |
| 2005/0181449 A1 | 8/2005 | Kozlowski |
| 2005/0261232 A1 | 11/2005 | Strong et al. |
| 2005/0287113 A1 | 12/2005 | Zalipsky |
| 2006/0292137 A1 | 12/2006 | Raines et al. |
| 2007/0166278 A1 | 7/2007 | Veronese |
| 2008/0025964 A1 | 1/2008 | Kink |
| 2008/0095755 A1 | 4/2008 | Kink |

FOREIGN PATENT DOCUMENTS

| | | |
|---|---|---|
| JP | 2003-206236 | 7/2003 |
| WO | 97/38134 | 10/1997 |
| WO | 98/33941 | 10/1997 |
| WO | 99/02685 | 1/1999 |
| WO | 99/07724 | 2/1999 |
| WO | 0009675 A1 | 2/2000 |
| WO | 0012738 A1 | 3/2000 |
| WO | WO 00/31242 | 6/2000 |
| WO | 01/94547 | 12/2001 |
| WO | 02/02630 | 1/2002 |
| WO | 03/031581 | 4/2003 |
| WO | WO 2007/149594 | 12/2007 |

OTHER PUBLICATIONS

Gorman, C., et al. "The Hype and the Hope" Time. 1998, 151(19) pp. 40-44. Included HTML referenced pp. 1-9.*

Gura, T "Systems for Identifying New Drugs are Often Faulty", Science. 1997, 278 (Nov. 7), pp. 1041-1042.*

Dermer, GB "Another Anniversary for the War on Cancer" Bio/Technology. 1994, 12(Mar), p. 320.*

McKie, R. "Cancer Research Set Back a Decade" The Observer. 2001, (Jun. 10), pp. 1-4 (HTML text).*

Nguyen, D.M., et al. Ann. Thorac. Surg. 1996, 62, pp. 109-114 (HTML text, 10 pages).*

Reddi, K.K., "Nature and Origin of Human Serum Ribonuclease" Biochem. Biophys. Res. Commun. 1975, 67(1), pp. 110-118.*

Potenza, N; Salvatore, V.; Migliozzi, A.; Martone, V.; Nobile, V; and Russo, A. "Hybridase activity of human ribonuclease-1 revealed by a real-time fluorometric assay" Nucleic Acids Research, 2006, 34(10), pp. 2906-2913.*

Dharap, S.S., et al., Journal of Controlled Release, (2003) 91, pp. 61-73.

Newton, D.L., et al., Blood, (2001) 97(2), pp. 528-535.

Hursey, M., et al., Leukemia & Lymphoma, (2002) 43(5), pp. 953-959.

Rybak, S., et al., Journal of Biological Chemistry, (1991) 266(31), pp. 21202-21207.

Newton, D.L., et al., Journal of Biological Chemistry, (1992) 267(27), pp. 19572-19578.

Jinno U.H., et al., Cancer Chemotherapy and Pharmacology, (1996) 38(4), pp. 303-308.

Yamamura, t., et al., European Journal of Surgery, (2002) 168(1), pp. 49-54.

Jinno H., et al., Life Sciences, (1996) 58(21), pp. 1901-1908.

Suzuki M., et al., Nature Biotechnology, (1999) 17, pp. 265-270.

Rubak S., et al., Cell Biophysics, (1992) 21(1-3), pp. 121-138.

Jinno H., et al., Anticancer Res., (2002) 22, pp. 4141-4146.

Stryer L. Biochemistry, 2nd Edition,(1981) pp. 17-21.

Gluzman Y., Cell, (1981) 23, pp. 175-182.

Gutte B., et al., Journal of Biological Chemistry, (1971) 246(6), pp. 1922-1941.

Narang S., Tetrahedron Report, (1983) 39(1), pp. 3-22.
Itakura K., et al., Recombinant DNA, Cleveland Symposium, (1981) pp. 273-289.
Itkaura K., et al., Ann. Rev. Biochem., (1984) 53, pp. 323-356.
Itkaura K., et al., Science, (1984) 198, pp. 1056-1063.
Ike Y., et al., Nucleic Acids Research, (1983) 11(2), pp. 477-488.
Scott J., et al., Science, (1990) 249, pp. 386-390.
Roberts B., et al., Proc. Natl. Acad. Sci., (1992) 89, pp. 2429-2433.
Devlin J., et al., Science, (1990) 249, 404-406.
Cwirla S., et al., Proc. Natl. Acad. Sci., (1990) 87, pp. 6378-6382.
Moore J., et al., Nature Biotechnology, (1996) 14, pp. 458-467.
Leung D., et al., Technique, (1989) 1(1), pp. 11-15.
Eckert K., et al., PCR Methods and Applications, (1991) 1(1), pp. 17-24.
Cadwell R.C., et al., PCR Methods and Applications, (1992) 1(4), pp. 28-33.
Zhao H., et al., Nucleic Acids Research,(1997) 25(6), pp. 1307-1308.
Smith G., Nature, (1994) 370, pp. 324-325.
Stemmer W., Nature, (1994) 370, pp. 389-391.
Stemmer W., Proc. Natl. Acad. Sci., (1994) 91, pp. 10747-10751.
Crameri A., et al., Nature Biotechnology, (1996)14, pp. 315-319.
Zhang J., et al., Proc. Natl. Acad. Sci., (1997) 94, pp. 4504-4509.
Crameri a., et al., Nature Biotechnology, (1997) 15, pp. 436-438.
Mcgrath M., et al., Cancer Research, (2003) 63, pp. 72-79.
Leland P., et al., Journal of Biological Chemistry, (2001) 276(46), pp. 43095-43102.
Futami J., et al., Protein Engineering, (1999) 12(11) pp. 1013-1018.
Zhang J., et al, Nucleic Acids Res., (2003) 31, pp. 602-607.
Zhang J., et al, Nucleic Acids Res., (2002) 30, pp. 1169-1175.
De Lorenzo, C., Cancer Res., (2004) 64, pp. 4870-4874.
Pous J., et al, Acta Crystallogr D Biol Crystallogr., (2001) 57, pp. 498-505.
Pous J., et al, J Mol. Biol., (2000) 303, pp. 49-60.
Rosenberg H, et al, Nucleic Acids Research, (1994) 24, pp. 3507-3513.
Harder J., et al, J. Biol. Chem., (2002) 277, pp. 46779-46784.
Bretscher, et al., J Biol. Chem., (2000) 275, 9893-9896.
Swaminathan G., et al, Biochemistry, (2002) 41, pp. 3341-3352.
Mosimann S.C., et al, J. Mol. Biol., (1996) 260, pp. 540-552.
Iyer S., et al, J Mol. Biol., (2005) 347, pp. 637-655.
Mohan C.G., et al, Biochemistry, (2002) 41, pp. 12100-12106.
Krasnykh V, et al, J Virology, (1998) 72, pp. 1844-1852.
Mclane K, Proc. Natl. Acad. Sci., (1995) 92, pp. 5214-5218.
Mitchell et al., Molec. Simul. (2004) 30, pp. 97-106.
Ban et al., Proc. 8th Ann. Intl. Conf. Res. Comp. Mol.Biol., (2004) pp. 205-212.
Boix E., et al Biochemistry, (1999) 38, pp. 16794-16801.
Mallorqui-Fernandez, G., et al J. Mol. Biol., (2000) 300, pp. 1297-1307.
Terzyan S.S., et al, J Mol. Biol., (1999) 285, pp. 205-214.
Leonidas D.D., et al, J. Mol. Biol., (1999) 285, pp. 1209-1233.
Leonidas D.D., et al, Protein Sci., (2001) 10, pp. 1669-1676.
Papageorgiou a.C., et al EMBO J., (1997) 16, pp. 5162-5177.
Shapiro, R., et al J. Mol. Biol., 302, pp. 497-519 (2000).
Raines, R.T., et al., J. Biol. Chem, 273, pp. 34134-34138 (1998).
Fisher, B.M., et al., Biochemistry, 37, pp. 12121-12132 (1998).
Gaur, D., et al., J. Biol. Chem., 276, pp. 24978-24984 (2001).
Bosch, M., et al., Biochemistry, 43, pp. 2167-2177 (2004).
Lin, M.C., J. Biol. Chem., 245, pp. 6726-6731 (1970).
Bal, H., et al, Eur. J. Biochem., 245, pp. 465-469 (1997).
Gaur, D., et al., Mol. Cell. Biochem., 275, 95-101 (2005).
Benito, A., et al., Protein Eng., 15, pp. 887-893 (2002).
Ribo, M., et al., Biol. Chem. Hoppe-seyler, 375, pp. 357-363 (1994).
Di Gaetano, G., et al., Biochem. J., 358, pp. 241-247 (2001).
Trautwein, K. et al., FEBS Lett., 281, pp. 275-277 (1991).
Curran, T.P., et al., Biochemistry 32, pp. 2307-2313 (1993).
Sorrentino, S., et al., Biochemistry 42, pp. 10182-10190 (2003).
Hamachi, I., et al., Bioorg. Med. Chem .Lett., 9, pp. 1215-1218 (1999).
Goldberg, J.M., et al, Proc. Natl. Acad. Sci., 96, pp. 2019-2024 (1999).
Asai, T., et al., J Immun. Meth., 299, 63-76 (2005).
Backer, M.V., et al., J Cont. Release, 89, pp. 499-511 (2003).

Backer, M.V., et al., Bioconj Chem, 15, 1021-1029 (2004).
Leland, P.S., et al., Proc. Natl. Acad. Sci., 95, pp. 10407-10412 (1998).
Strong, Laura E, et al., "Human ribonuclease variants with broad anti-cancer activity," 2006, Am Assoc for Cancer Res Annual Mtg, 47, P514.
Piccoli, Renate et al., "A dimeric mutant of human pancreatic ribonuclease with selective cytotoxicity toward malignant cells," 1999, Pro Nat Acad Sci, 96, pp. 7768-7773.
Strong, L E et al., "408 Poster Human RNase 1 variants are effective anti-cancer agents," 2006, EP J Cancer Supp, Pergamon, Oxford, GB, 4, p. 125.
Matousek J, "Ribonucleases and their antitumor activity," 2001, Comp Biochem Physiology Tox Pharma, 129, pp. 175-191.
Rosenberg H F et al., "Eosinophils, Eosinophil Ribonucleases, and their Role in Host Defense Against Respiratory Virus Pathogens," 2001, J Leukocyte Bio, Fed Am Soc Exper Bio, 70, pp. 691-698.
Leland, P.A. et al., "Cancer Chemotherapy—Ribonucleases to the Rescue," Chem and Biology. Apr. 2001, 8:405-413.
Merlino, A., et al., "The importance of Dynamic Effects on the Enzyme Activity X-ray Structure and Molecular Dynamics of Onconase Mutants," J Biol Chem 2005, 280:17953-17960.
Domachowske et al., "Evolution of antiviral activity in the ribonuclease a gene superfamily . . . ," Nucleic Acids Res 26 (23): 5327-32 (1998).
Sorrentino and Glitz, "Ribonuclease activity and substrate preference of human eosinophil cationic protein (ECP)"1991 FEBS Lett. 288:23-6.
Kobe, et al. "Mechanism of ribonuclease inhibition by ribonuclease inhibitor protein based on the crystal structure of ts complex with ribonuclease A," J Mol Biol, 1996, 264:1028-43.
Dickson, K A, et al., "Compensating effects on the cytotoxicity of ribonuclease A variants," 2003 Archives Biochem and Biophysics, Acad Press, 415:172-177.
Klink ,T A, et al., "Conformational stability is a determinant of ribonuclease A cytotoxicity," 2000, J Biolog Chem, 275:17463-17467.
Psarras, K, et al., "Human pancreatic RNase1-human epidermal growth factor fusion: An entirely human immunotoxin analog with cytotoxic properties against squamous cell carcinomas," Protein Eng, 1998, 11:1285-1292.
March, Advanced Organic Chemistry: Reactions Mechanisms and Structure, 4th E. (New York: Wiley-Interscience, 1992)—Book, 1495 pages.
Binkley et al., "RNA ligands to human nerve growth factor ," 1995 Nuc Acids Res 23(16):3198-205.
Capala et al., "Boronated Epidermal Growth Factor as a Potential Targeting Agent for Boron Neutron Capture Therapy of Brain Tumors," 1996 Bioconjugate Chem 7:7-15.
Francis et al., Stability of protein pharmaceuticals: in vivo pathways of degradation and strategies for protein stabilization (Eds. Ahern., T. and Manning, M.C.) Plenum, N.Y., pp. 247-251 (1991).
Haldar et al., "Bcl2 Is the Guardian of Microtubule Integrity," 1997 Cancer Research 57:229-233.
Hanisch et al., "Structural studies on oncofetal carbohydrate antigens (Ca 19-9, Ca 50, and Ca 125) carried by O-linked sialyloligosaccharides on human amniotic mucins," 1988 Carbohydr Res 178:29-47.
Hinoda et al., "Immunochemical characterization of adenocarcinoma-associated antigen yh206," 1988 Cancer J 42:653-658.
Ishida et al., "Related Glycoproteins from Normal Secretory and Malignant Breast Cells," 1989 Tumor Biol 10:12-22.
Jellinek et al., "Inhibition of receptor binding by high-affinity RNA ligands to vascular endothelial growth factor," 1994 Biochem 33(34):10450-6.
Kinstler et al., "Mono-N-terminal poly(ethylene glycol)—protein conjugates," 2002 Advanced Drug Delivery Reviews 54:477-485.
Kirpotin et al., "Sterically Stabilized Anti-HER2 Immunoliposomes: Design and Targeting to Human Breast Cancer Cells in Vitro," 1997 Biochem 36:66.
Kjeldsen et al., "Preparation and Characterization of Monoclonal Antibodies Directed to the Tumor-associated O-linked Sialosyl-2- . . . ," 1988 Cancer Res 48:2214-2220.

Kozlowski A, et al., "Development of pegylated interferons for the treatment of chronic hepatitis C." 2001 BioDrugs, 15:419-429.

Lan et al., "Isolation and properties of a human pancreatic adenocarcinoma-associated . . .,"1985 Cancer Res 45:305-310.

Lanni et al., "p53-independent apoptosis induced by paclitaxel through an indirect mechanism," 1997 Proc Natl Acad Sci 94:9679-9683.

Laznicek, et al. "Pharmacokinetics and Distribution of Ribonuclease and its Monomethoxypoly(Ethylene Glycol) Derivatives in Rats" Pharmacological Research, vol. 28, No. 2, Sep. 1, 1993, pp. 153-162.

Matousek et al. "PEG chains increase aspermatogenic and antitumor activity of RNase A and BS-RNase enzymes" Journal of Controlled Release 82 (2002) 29-37.

Matousek, et al. "Effect of hyaluronidase and PEG chain conjugation on the biologic and antitumor activity of RNase A" Journal of Controlled Release, vol. 94, No. 2-3, Feb. 10, 2004, pp. 401-410.

Michaelis, et al. "Coupling of the antitumoral enzyme bovine seminal ribonuclease to polyethylene glycol chains increases its systemic efficacy in mice" Anti-Cancer Drugs, vol. 13, No. 2, Feb. 2002, pp. 149-154.

Miller, K.D. and Sledge, G.W. Jr, "Taxanes in the treatment of breast cancer: a prodigy comes of age,"1999 Cancer Investigation, 17:121-136.

Milton Harris J et al: "Effect of Pegylation on Pharmaceuticals" Nature Reviews. Drug Discovery, vol. 2, No. 3, Mar. 1, 2003, pp. 214-221.

Ottl et al., "Preparation and Photoactivation of Caged Fluorophores and Caged Proteins Using a New Class of Heterobifunctional, Photocleavable Cross-Linking Reagents,"1998 Bioconj Chem 9:143-151.

Park et al., "Anti-HER2 immunoliposomes for targeted therapy of human tumors," 1997 Cancer Lett 118:153-160.

Pegram et al., 1995 Am Soc Clin Oncol 14:106.

Pouckova, et al. "Polymer-conjugated bovine pancreatic and seminal ribonucleases inhibit growth of human tumors in nude mice" Journal of Controlled Release, vol. 95, No. 1, Feb. 20, 2004, pp. 83-92.

Press et al., "Expression of the HER-2/neu proto-oncogene in normal human adult and fetal tissues," 1990 Oncogene 5:953-62.

Roberts et al. "Chemistry for peptide and protein PEGylation," 2002 Advanced Drug Delivery Reviews 54:459-476.

Skerra, et al., "Engineered protein scaffolds for molecular recognition," J Mol Recognit. 2000, 13:167-87.

Springer, et al., "Blood group Tn-active macromolecules from human carcinomas and erythrocytes: characterization of and specific reactivity with mono- and poly-clonal anti-Tn antibodies induced by various immunogens," 1988 Carbohyd Res 178:271-292.

Tjandra, et al., "Application of mammary serum antigen assay in the management of breast cancer: A preliminary report," 1988 J Surg 75:811-817.

Tortora et al., "Synergistic Inhibition of Growth and Induction of Apoptosis by 8-Chloro-cAMP and Paclitaxel or Cisplatin in Human Cancer Cells," 1997 Cancer Res 57:5107-5111.

Tuerk et al., "In vitro evolution of functional nucleic acids : high-affinity RNA ligands of HIV-1 proteins," 1993 Gene 137:33-9.

Vasey et al., "Phase I Clinical and Pharmacokinetic Study of PK1 [N-(2-Hydroxypropyl) methacrylamide Copolymer Doxorubicin] . . . ," 1999 Clin Cancer Res 5:83-94.

Veronese I "Surface Modification of Proteins" Applied Biochemistry and Biotechnology, vol. 11, 1985, pp. 141-152.

Veronese II "Peptide and protein PEGylation: a review of problems and solutions" Biomaterials 22 (2001) 405-417.

Zaffaroni et al., "Induction of apoptosis by taxol and cisplatin and effect on cell cycle-related proteins in cisplatin-sensitive and—resistant human ovarian cancer cells," 1998 Brit. J. Cancer 77:1378-1385.

Zalipsky, "Functionalized Poly(ethylene glycol) for Preparation of Biologically Relevant Conjugates," Bioconjugate Chem 6, 150-165 (1995).

Zhou, et al., "Selection of Antibiotic-Resistant Bacterial Mutants: Allelic Diversity among Fluoroquinolone-Resistant Mutations," 2000 JID 182:517-525.

Lavis et al., "Tuning the pKa of Flourescein to Optimize Binding Assays," 2007 Anal Chem, 79:6775-6782.

Wang, "An exact mathematical expression for describing competitive binding of two different ligands to a protein molecule", 1995 FEBS Lett 360: 111-114.

Roehrl et al., "A General Framework for Development and Data Analysis of Competitive High-Throughput Screens for Small-Molecule Inhibitors of Protein-Protein Interactions by Fluorescence Polarization," 2004 Biochem 43: 16056-16066.

Kelemen et al., "Hypersensitive substrate for ribonucleases", 1999 Nucl Acids Res, 27: 3696-3701.

Smith et al., "Potent Inhibition of Ribonuclease A by Oligo(vinylsulfonic Acid)", 2003 J Biol Chem 278:20934-30938.

Del Cardayre & Raines, "Structural Determinants of Enzymatic Processivity", 1994 Biochem 33:6031-6037.

Deonarain, M.P. et al., "Targeting enzymes for cancer therapy: Old Enzymes in New Roles." British Journal of Cancer, Nov. 1994 70(5):786-794.

References cited in corresponding Japanese Office Action dated Mar. 7, 2011, JP Application No. 2007-508473; 2 pages.

Davis et al., Basic Methods in Molecular Biology. (1986), 388 pages.

Martin, Remington's Pharmaceutical Sciences, 15th Ed. Mack Publ. Co., Eason, Pa. (1975)-Book, 1957 pages.

* cited by examiner

Efficacy of agents against A549 cell line

Toxicity of agents reflected by changes in body weight

Efficacy of agents against
A549 cell line

Toxicity of agents reflected
by changes in body weight

FIGURE 15

| AA# | RNase 1 | RNase 2 | RNase 3 | RNase 4 | RNase 5 | RNase 6 | RNase 7 | RNase 8 |
|---|---|---|---|---|---|---|---|---|
|  | - | K + | R + |  |  | W | K | K |
|  | - | P + | P + |  |  | P | P | P |
| 1 | K + | P + | P + | Q 0 (a1) | Q + | K | K | K |
| 2 | E + | Q + | Q + | D 0 (a1) | D + | R | G | D |
|  | - | F + (dis) | F + | - | N 0 (a1) | L | M | M |
| 3 | S + | T + | T + | G 0 (a1) | S 0 (a1) | T | T | T |
| 4 | R 0 (a1) | W + (a1, RI) | R 0 (a1) | M 0 (a1) | R 0 (a1, RI, P2) | K | S | S |
| 5 | A 0 (a1) | A 0 (a1) | A 0 (a1) | Y 0 (a1) | Y 0 (a1) | A | S | S |
| 6 | K 0 (a1) | Q 0 (a1) | Q 0 (a1) | Q 0 (a1) | T 0 (a1) | H | Q | Q |
| 7 | K 0 (a1) | W — (a1, P2) | W 0 (a1) | R 0 (a1) | H + (a1, RI) | W | W | W |
| 8 | F 0 (a1) | F 0 (a1) | F 0 (a1) | F 0 (a1) | F 0 (a1) | F | F | F |
| 9 | Q 0 (a1) | E 0 (a1) | A 0 (a1) | L 0 (a1) | L 0 (a1) | E | K | K |
| 10 | R 0 (a1) | T — (a1, P2) | I 0 (a1) | R 0 (a1) | T 0 (a1) | I | I | T |
| 11 | Q 0 (a1) | Q 0 (a1) | Q — (P1, a1) | Q — (a1, P1) | Q 0 (a1, RI, P1) | Q | Q | Q |
| 12 | H — (P1, a1) | H — (P1, a1) | H — (P1, a1) | H — (P1, a1) | H — (P1, a1) | H— (P1) | H— (P1) | H— (P1) |
| 13 | M + | I + | I | V + | Y + | I | M | V |
| 14 | D + | N + | S | H + | D + | Q | Q | Q |
| 15 | S + | M + | L | P + | A + | P | P | P |
| 16 | D + | T + | N | E + | K + | S | S | S |

FIGURE 15, CONT'D

| | | | | | | | | |
|---|---|---|---|---|---|---|---|---|
| 17 | S + | S + | P | E + | - | P | P | P |
| 18 | S + | Q + | P | Y + | P + | L | Q | Q |
| 19 | P + | Q + (RI, dis) | R | - | Q + | Q | A | A |
| 20 | S + | - | - | G + | G + | - | - | - |
| 21 | S + | - | - | G + | R + | - | - | - |
| 22 | S + | - | - | S + | D + | - | - | - |
| 23 | S + | - | - | D 0 (a2) | D 0 (a2) | - | - | - |
| 24 | T + | - | - | R 0 (a2) | R + (a2, RI) | - | - | - |
| 25 | Y 0 (a2) | - | - | Y 0 (a2) | Y 0 (a2) | - | - | - |
| 26 | C - (a2, disulf) | C — (a2, disulf) | C — (disulf, a2) | C — (a2, disulf) | C — (a2, disulf) | C | C | C |
| 27 | N 0 (a2) | T 0 (a2) | T 0 (a2) | N 0 (a2) | E 0 (a2) | N | N | N |
| 28 | Q 0 (a2) | N + (a2, RI, dis) | I 0 (a2) | L 0 (a2) | S 0 (a2) | R | S | S |
| 29 | M 0 (a2) | A 0 (a2) | A 0 (a2) | M 0 (a2) | I 0 (a2) | A | A | A |
| 30 | M 0 (a2) | M 0 (a2) | M 0 (a2) | M 0 (a2) | M 0 (a2) | M | M | M |
| 31 | R + (a2, RI) | Q 0 (a2) | R 0 (a2) | Q 0 (a2) | R + (a2, RI) | S | K | S |
| 32 | R + (a2, RI) | V 0 (a2) | A 0 (a2) | R 0 (a2) | R + (a2, RI) | G | N | I |
| 33 | R + | I 0 (a2, dis) | I 0 (a2) | R + | R + | I | I | I |
| 34 | N + | N 0 (a2) | N 0 (a2) | K + | G + | N | N | N |
| 35 | M + | N + (a2, RI, dis) | N + | M + | L + | N | K | K |
| 36 | T + | Y 0 (a2) | Y + | T + | T + | Y | H | Y |
| 37 | Q + (RI) | Q + (a2, RI) | R 0 (P-1) | L + | - | T | T | T |

FIGURE 15, CONT'D

| | | | | | | | | |
|---|---|---|---|---|---|---|---|---|
| 38 | G + (RI) | R + (RI) | W + | Y + | S + (RI) | Q | K | E |
| 39 | R + | R 0 (P-1, RI) | R + | H + | P + (RI) | H | R | R |
| 40 | C — (disulf) | C — (disulf) | C — (disulf) | C — (disulf) | C — (disulf) | C | C | C |
| 41 | K — (enz) | K — (enz, P1) | K — (P1) | K — (enz, P1) | K — (enz, P1, RI) | K | K | K |
| 42 | P 0 | N 0 (P-1, RI) | N + | R | D + (RI) | H | D | D |
| 43 | V 0 (b1) | Q — (P-1) | Q 0 (b1) | F 0 (b1) | I — (b1, B1) | Q | L | L |
| 44 | N 0 (b1) | N 0 (b1) | N 0 (b1) | N 0 (b1) | N — (b1, B1) | N | N | N |
| 45 | T 0 (b1) | T (b1, B1) | T — (b1, B1) | T 0 (b1) | T — (b1, B1) | T | T | T |
| 46 | F 0 (b1) | F 0 (b1) | F 0 (b1) | F 0 (b1) | F 0 (b1) | F | F | F |
| 47 | V 0 (b1) | L 0 (b1) | L 0 (b1) | I 0 (b1) | I 0 (b1) | L | L | L |
| 48 | H + | L + | R + | H + | H + | H | H | H |
| 49 | E+ | T + | T + | E + | G + | D | E | E |
| 50 | P+ | T | T + | D + | N | S | P | P |
| 51 | L 0 (a3) | F 0 (a3) | F 0 (a3) | I 0 (a3) | K 0 (a3) | F | F | F |
| 52 | V 0 (a3) | A 0 (a3) | A 0 (a3) | W 0 (a3) | R 0 (a3) | Q | S | S |
| 53 | D 0 (a3) | N 0 (a3) | N 0 (a3) | N 0 (a3) | S 0 (a3) | N | S | S |
| 54 | V 0 (a3) | V 0 (a3) | V 0 (a3) | I 0 (a3) | I 0 (a3) | V | V | V |
| 55 | Q 0 (a3) | V 0 (a3) | V 0 (a3) | R 0 (a3) | K 0 (a3) | A | A | A |
| 56 | N 0 (a3) | N + (a3, dis) | N 0 (a3) | S 0 (a3) | A 0 (a3) | A | A | I |

FIGURE 15, CONT'D

| | | | | | | | | |
|---|---|---|---|---|---|---|---|---|
| 57 | V 0 (a3) | V 0 (a3) | V + | I 0 (a3) | I 0 (a3) | V | T | T |
| 58 | C — (disulf) | C — (disulf, a3) | C — (disulf) | C — (disulf, a3) | C — (disulf, a3) | C | C | C |
| 59 | F 0 (a3) | G 0 (a3) | G | S + | E 0 (rec) | D | Q | Q |
| 60 | Q + | N + | N | T + | N 0 (rec) | L | T | T |
| 61 | E 0 (b2) | P + | Q | T + | K 0 (rec) | L | P | P |
| 62 | K 0 (b2) | N + | S | N + | N 0 (rec, b2) | S | K | N |
| 63 | V 0 (b2) | M + | I | I + | G 0 (rec, b2) | I | I | I |
| 64 | T 0 (b2) | T + | R | Q + | N 0 (rec, b2) | V | A | A |
| 65 | C — (disulf) | C — (disulf) | C — (disulf) | C — (disulf) | P 0 (rec, b2) | C | C | C |
| 66 | K + | P + | P | K + | H 0 (rec, b2) | K | K | K |
| 67 | N + (RI) | S 0 (P0, RI, dis) | H | N + | R 0 (b2) | N | N | N |
| 68 | G + | N + (RI) | N | G + | E 0 (rec, RI) | R | G | S |
| 69 | Q + | K + | R | K + | N 0 (rec) | R | D | C |
| 70 | G + | T + | T | M + | L 0 (b3) | - | - | - |
| | - | R 0 (B2, RI, dis) | L | - | - | - | - | - |
| | - | K + | N | - | - | H | K | K |

FIGURE 15, CONT'D

| | | | | | | | | |
|---|---|---|---|---|---|---|---|---|
| 71 | N + | N 0 (B2, RI) | N — (B2) | N + | R 0 (b3) | N | N | N |
| 72 | C — (b3, disulf) | C — (b2, disulf) | C — (disulf, b2) | C — (b2, disulf) | I 0 (b3) | C | C | C |
| 73 | Y 0 (b3) | H 0 (b2) | H 0 (b2) | H 0 (b2) | S 0 (b3) | H | H | H |
| 74 | K 0 (b3) | H 0 (b2) | R 0 (b2) | - | K + | Q | Q | Q |
| 75 | S+ | S + | S + | - | S + | S | S | S |
| 76 | N+ | G + | R + | E 0 (b2) | S + | S | H | H |
| 77 | S+ | S + | F + | G 0 (b2) | - | K | G | G |
| 78 | S + | Q + | R + | V 0 (b2) | - | P | A | P |
| 79 | M 0 (b4) | V 0 (b3) | V 0 (b3) | V 0 (b2) | F 0 (b4) | V | V | M |
| 80 | H 0 (b4) | P 0 (b3) | P 0 (b3) | K 0 (b2) | Q 0 (b4) | N | S | S |
| 81 | I 0 (b4) | L 0 (b3) | L 0 (b3) | V 0 (b2) | V 0 (b4) | M | L | L |
| 82 | T 0 (b4) | I 0 (b3) | L 0 (b3) | T 0 (b2) | T 0 (b4) | T | T | T |
| 83 | D 0 (b4) | H — (B1) | H 0 (b3) | D — (b2, B1) | T — (b4, B1) | D | M | M |
| 84 | C — (b4, disulf) | C — (disulf, b3) | C — (disulf) | C — (disulf) | C — (disulf, b4) | C | C | G |
| 85 | R 0 (b4) | N + (b3, RI) | D 0 (b3) | R 0 (b2) | K 0 (b4) | R | K | E |
| 86 | L 0 (b4) | L + (b3, RI) | L 0 (b3) | D 0 (b2) | L 0 (b4) | L | L | L |
| 87 | T + | T + (b3, RI) | I + | T + | H + (b4, RI) | T | T | T |
| 88 | N + | T + (b3, RI) | N + | G + | G + (RI) | S | S | S |
| 89 | G + | P + (RI) | P + | S + | G+ (RI) | G | G | G |

FIGURE 15, CONT'D

| | | | | | | | | |
|---|---|---|---|---|---|---|---|---|
| 90 | S + | S + | G + | S + | S + (RI) | - | - | - |
| 91 | R + | P + | A + | R + | P + (RI) | - | - | - |
| | - | Q + | Q + | - | - | - | - | - |
| | - | N + | N + | - | - | K | K | K |
| 92 | Y + | I + (RI) | I + | A + | W + (RI) | Y | H | Y |
| 93 | P + | S + (RI) | S + | P + | P + | P | P | P |
| 94 | N + | N + | N + | N + | P + | Q | N | N |
| 95 | C — (disulf) | C — (disulf) | C — (disulf) | C — (disulf) | C — (disulf) | C | C | C |
| 96 | A 0 | R 0 (b4) | R + | R + | Q + (b5, RI) | R | R | R |
| 97 | Y 0 (b5) | Y 0 (b4) | Y 0 (b4) | Y 0 (b3) | Y 0 (b5) | Y | Y | Y |
| 98 | R 0 (b5) | A 0 (b4) | A 0 (b4) | R 0 (b3) | R + (b5, RI) | S | K | K |
| 99 | T 0 (b5) | Q 0 (b4) | D 0 (b4) | A 0 (b3) | A 0 (b5) | A | E | E |
| 100 | S 0 (b5) | T 0 (b4) | R 0 (b4) | I 0 (b3) | T 0 (b5) | A | K | K |
| 101 | P 0 (b5) | P 0 (b4) | P 0 (b4) | A 0 (b3) | A 0 (b5) | A | R | H |
| 102 | K 0 (b5) | A 0 (b4) | G 0 (b4) | S 0 (b3) | G 0 (b5) | Q | Q | L |
| 103 | E 0 (b5) | N 0 (b4) | R 0 (b4) | T 0 (b3) | F 0 (b5) | Y | N | N |
| 104 | R 0 (b5) | M 0 (b4) | R 0 (b4) | R — (b3, B1) | R 0 (b5) | K | K | T |
| 105 | H + | F + | F + | R — (b3, B1) | N + | F | S | P |
| 106 | I 0 (b6) | Y 0 (b5) | Y 0 (b5) | V 0 (b3) | V + | F | Y | Y |
| 107 | I 0 (b6) | I 0 (b5) | V 0 (b5) | V 0 (b3) | V 0 (b6) | I | V | I |
| 108 | V 0 (b6) | V 0 (b5) | V 0 (b5) | I 0 (b3) | V 0 (b6) | V | V | V |

FIGURE 15, CONT'D

| | | | | | | | | |
|---|---|---|---|---|---|---|---|---|
| 109 | A 0 (b6) | A 0 (b5) | A 0 (b5) | A 0 (b3) | A + (b6, RI) | A | A | A |
| 110 | C — (disulf, b6) | C— (disulf, b5) | C— (disulf, b5) | C — (disulf, b3) | C — (disulf, b6) | C | C | C |
| 111 | E 0 (b6) | D—(B2, RI, b5) | D 0 (b5) | E 0 (b3) | E — (b6, RI, B2) | D | K | D |
| 112 | G + | N 0 (b5) | N— (B2, b5) | G + | N + | P | P | P |
| 113 | S + | R + | R + | N + | G + | P | P | P |
| | - | D + | D + | - | - | - | - | - |
| | - | Q + | P + | - | - | Q | Q | Q |
| | - | R + | R + | - | - | K | K | Q |
| | - | R + | - | - | - | S | K | G |
| | - | D + | D + | - | - | D | D | D |
| | - | P + | S + | - | - | P | S | P |
| | - | P + | P + | - | - | P | Q | G |
| | - | Q + | R + | - | - | - | Q | - |
| | - | Y + | Y + | - | - | Y | F | Y |
| 114 | P + | P + | P + | P + | - | K | H | P |
| 115 | Y + | V 0 (b6) | V 0 (b6) | Q + | - | L | L | L |
| 116 | V 0 (b7) | V 0 (b6) | V 0 (b6) | V 0 (b4) | L 0 (b7) | V | V | V |
| 117 | P 0 (b7) | P 0 (b6) | P 0 (b6) | P 0 (b4) | P 0 (b7) | P | P | P |
| 118 | V 0 (b7) | V + (b6, RI) | V 0 (b6) | V 0 (b4) | V 0 (b7) | V | V | V |
| 119 | H — (P1, b7) | H — (P1, RI, b6) | H— (P1, B2, b6) | H — (P1, b4) | H — (P1, b7) | H | H | H |
| 120 | F 0 (b7) | L — (b6, B1) | L— (B1, b6) | F 0 (b4) | L — (b7, B1) | L | L | L |
| 121 | D 0 (b7) | D 0 (b6) | D 0 (b6) | D 0 (b4) | D + | D | D | D |
| 122 | A 0 (b7) | R 0 (b6) | T 0 (b6) | G — (b4, P1) | Q + (a, RI) | S | R | K |

FIGURE 15, CONT'D

| | | | | | | | |
|---|---|---|---|---|---|---|---|
| 123 | S 0 (b7) | I — (b6, B1) | T— (B1, b6) | - | S 0 (a) | I | V | V |
| 124 | V 0 (b7) | I + | I 0 (b6) | - | I 0 (a) | L | L | V |
| 125 | E 0 (b7) | - | - | - | F 0 (a) | - | - | - |
| 126 | D 0 (b7) | - | - | - | R + | - | - | - |
| 127 | S + | - | - | - | R + | - | - | - |
| 128 | T + | - | - | - | P + | - | - | - |

SEQUENCE LISTING

<160> NUMBER OF SEQ ID NOS: 1

<210> SEQ ID NO 1

```
-continued

<211> LENGTH: 128
<212> TYPE: PRT
<213> ORGANISM: Homo sapiens

<400> SEQUENCE: 1

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
            115                 120                 125
```

METHODS AND COMPOSITIONS FOR THE TREATMENT OF CANCER

The present application claims priority to U.S. Provisional Patent Application Ser. No. 60/831,378, filed Jul. 17, 2006, herein incorporated by reference in its entirety.

FIELD OF THE INVENTION

The present invention is directed toward the delivery of toxic agents to pathogenic cells, particularly cancer cells. In some embodiments, the toxic agent is a human ribonuclease or similar agent that is toxic to cells.

BACKGROUND OF THE INVENTION

The term "chemotherapy" simply means the treatment of disease with chemical substances. The father of chemotherapy, Paul Ehrlich, imagined the perfect chemotherapeutic as a "magic bullet;" such a compound would kill invading organisms or cells without harming the host. While significant progress has been made in identifying compounds that kill or inhibit cancer cells and in identifying methods of directing such compounds to the intended target cells, the art remains in need of improved anti-cancer compounds and therapies.

SUMMARY OF THE INVENTION

The present invention is directed toward the delivery of a toxic protein or related agent to pathogenic cells, particularly cancer cells. In some embodiments, the toxic protein is a human ribonuclease 1 or similar agent that is toxic to target cells. Experiments conducted during the development of the present invention showed that human ribonuclease finds use in cancer therapies, as well as use in research and diagnostic applications.

Accordingly, in some embodiments, the present invention provides wild type ribonuclease 1 (e.g., from human or other origin) compositions for use in killing cells and degrading RNA or otherwise providing cytotoxic activity, cytostatic activity, or cell damaging activity. The present invention also provides variant ribonuclease 1 having properties similar to wild type ribonuclease 1. The present invention further provides therapies comprising a ribonuclease 1 in combination with conventional therapies and optionally a different (e.g., a non-natural or variant) ribonuclease.

For example, in some embodiments, the present invention provides a pharmaceutical composition comprising a wild type human ribonuclease 1 (human RNase 1) or variant thereof, wherein the composition is configured to kill a cell or otherwise affect target cells (e.g., cancer cells). In preferred embodiments, the human RNase 1 or variant thereof has one or more activities or properties of wild type human RNase 1 including, but not limited to, the ability to reduce tumor size in an animal, the ability to degrade RNA, lack of reduction in weight in animals administered the RNase, speed and accuracy of protein folding, minimal immunogenicity of cytotoxicity, and amenity to reduce symptoms of disease (e.g. cancer). In certain embodiments, the composition further comprises a non-natural human ribonuclease 1 (e.g., to be co-administered with the proteins of the present invention). In some embodiments, the non-natural human ribonuclease 1 has a variant sequence that disrupts binding to the ribonuclease inhibitor. In certain preferred embodiments, the non-natural human ribonuclease 1 has a variant sequence compared to a natural ribonuclease 1 including, but not limited to, L86E, N88R, G89D, R91D/R4C, L86E, N88R, G89D, R91D, V118C/L86E, N88C, R91D/R4C, L86E, N88C, R91D, V118C/R4C, N88C, V118C/K7A, L86E, N88C, R91D/K7A, L86E, N88R, G89D, R91D/R4C, K7A, L86E, N88C, R91D, V118C and R4C, K7A, L86E, N88R, G89D, R91D, V118C/G38R R39D L86E N88R G89D R91D and R4C, G89R, S90R, V118C.

In some embodiments, the composition further comprises a known therapeutic agent (e.g., a chemotherapy agent or an apparatus for providing radiation therapy). In some embodiments, the cell is a cancer cell, a cancer stem cell, a cell associated with an inflammatory response, a cell associated with an infection (e.g., by a virus) or a cell associated with an autoimmune disease.

The present invention further provides a pharmaceutical composition comprising a variant human ribonuclease 1 (variant human RNase 1) having an equivalent or similar activity of a wild-type human ribonuclease 1, wherein the RNase 1 is configured to kill a cell or otherwise affect target cells (e.g., cancer cells).

The present invention also provides a method for killing a cell or otherwise providing cytotoxic activity, cytostatic activity, or cell damaging activity, comprising the step of exposing a cell to a wild type or variant human ribonuclease (human RNase 1). In some embodiments, the cell resides in vitro. In other embodiments, the cell resides in vivo. In some embodiments, the cell is a cancer cell, a cancer stem cell, a cell associated with an inflammatory response or a cell associated with an autoimmune disease. In some embodiments, the cell resides in a subject suspected of having cancer. In certain embodiments, the method further comprises the step of providing a known therapeutic agent to the cell (e.g., a chemotherapeutic agent or radiation).

The present invention additionally provides a method for degrading RNA comprising the step of exposing a sample comprising the RNA to a wild type or variant human ribonuclease (human RNase 1). In some embodiments, the RNA resides in vitro. In other embodiments, the RNA resides in vivo. In certain embodiments, the RNA is viral in origin. In other embodiments, the viral RNA resides in a subject suspected of being infected.

DESCRIPTION OF THE FIGURES

FIG. 15 shows amino acid residues in human ribonucleases as well as sites modified or targeted for modification ("interest sites") located therein depicted as low interest (−), medium interest (0), or high interest (+) sites.

DEFINITIONS

Figure 1:
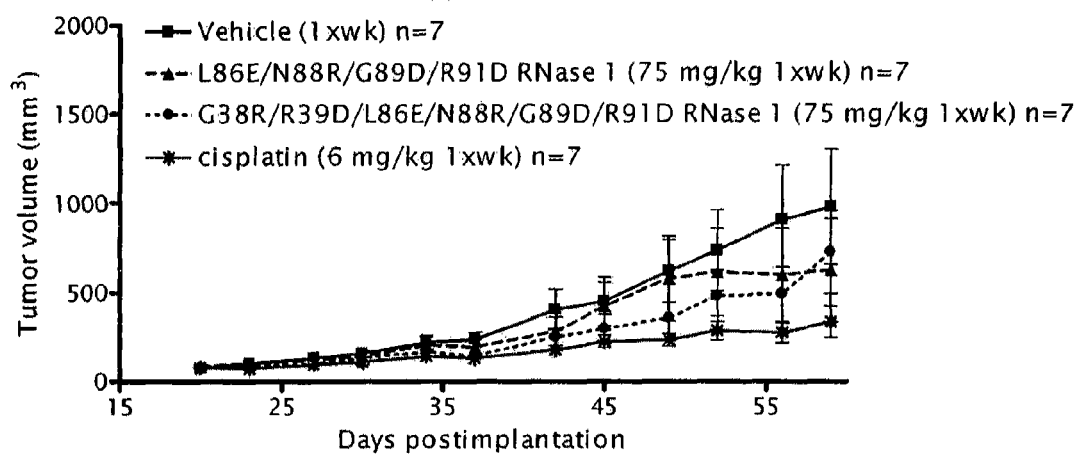
FIG. 1 shows in vivo activity of RNases in some embodiments of the present invention.
Figure 1:
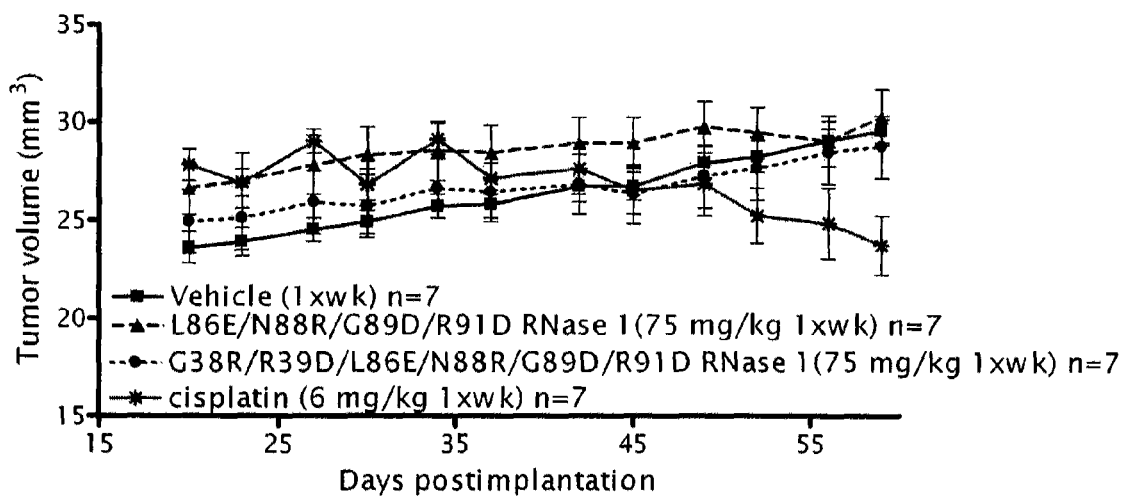

To facilitate an understanding of the present invention, a number of terms and phrases are defined below:

As used herein, the term "variant of human ribonuclease 1" refers to a human ribonuclease 1 that varies from SEQ ID NO:1 by at least one amino acid, yet remains homologous to wild-type human ribonuclease 1.

As used herein, the term "variant of human ribonuclease 1 that retains the activity of ribonuclease 1" refers to a variant of human ribonuclease 1 that retains enzymatic activities similar to that (e.g., that has at least 1%, at least 5%, at least 15%, at least 30%, at least 50%, at least 60%, at least 75%, at least 85%, at least 95%, or at least 99% of activity retained) associated with ribonuclease 1. Tests for measuring enzymatic activities are described herein and are known in the art.

As used herein, the term "variant of human ribonuclease 1 retaining RNA degradation activity" refers to a variant of human ribonuclease 1 (e.g., SEQ ID NO:1) that has at least 1%, at least 5%, at least 15%, at least 30%, at least 50%, at least 60%, at least 75%, at least 85%, at least 95%, or at least 99% of RNA degradation activity of wild type human ribonuclease 1. RNA degradation activity may be measured using any suitable assay including, but not limited to, visualization and quantitation of a degraded RNA sample using agarose or polyacrylamide gel electrophoresis. In some preferred embodiments, the variant has one or a limited number of amino acid substitutions (e.g., conservative or non-conservative substitutions), additions, or deletions (e.g., truncations) compared to wild type enzyme.

As used herein, the term "variant of human ribonuclease 1 having substantially the same cell killing activity, cytotoxic activity, cytostatic activity, or cell damaging activity" refers to a variant of human ribonuclease 1 (e.g., SEQ ID NO:1) that has at least 30%, at least 50%, at least 60%, at least 75%, at least 85%, at least 95%, or at least 99% of the cell killing activity, cytotoxic activity, cytostatic activity, or cell damaging activity of wild type human ribonuclease 1. For example, in some embodiments, the activity is the ability to kill or otherwise affect cancer cells. In other embodiments, it is the ability to reduce tumor size in animals. In yet other embodiments, the activity is the ability to reduce symptoms of a disease characterized by aberrant cell growth (e.g., cancer). Activity may be measured using any suitable method including, but not limited to, commercially available cell viability assays, measurement of tumor size, and commercially available cell proliferation assays. In some preferred embodiments, the variant has one or a limited number of amino acid substitutions (e.g., conservative or non-conservative substitutions), additions, or deletions (e.g., truncations) compared to wild type enzyme.

As used herein, the term "variant of human ribonuclease 1 retaining protein folding properties" refers to a variant of human ribonuclease 1 (e.g., SEQ ID NO:1) that exhibits similar protein folding properties as wild type human ribonuclease 1. Protein folding properties include speed of protein folding and folding of proper structure (folding that substantially retains the activity of wild-type ribonuclease 1). In preferred embodiments variants fold with at least 5%, at least 25%, at least 50%, at least 60%, at least 75%, at least 85%, at least 95%, or at least 99% or more of the speed of the wild type protein. Assays for protein folding are well known in the art and include, but are not limited to, spectroscopic and enzymatic (e.g. RNA degradation) assays and HPLC. In some preferred embodiments, the variant has one or a limited number of amino acid substitutions (e.g., conservative or non-conservative substitutions), additions, or deletions (e.g., truncations) compared to wild type enzyme.

As used herein, the term "variant of human ribonuclease 1 having similar immunogenicity properties" refers to a variant of human ribonuclease 1 (e.g., SEQ ID NO:1) that, in some embodiments, exhibits substantially the same or better immunogenicity properties as wild type human ribonuclease 1. Immunogenicity properties include toxicity and undesirable immune responses (e.g., cytotoxic immune response) in animals. In preferred embodiments, variants exhibit less than 100%, preferably less than 90%, even more preferably less than 80%, and still more preferably less than 70% of the toxicity or undesirable immune response of wild type human ribonuclease 1. The level of toxicity or immunogenicity can be determined using any suitable method including, but not limited to, commercially available assays for toxicity and immune response (e.g., measurement of cytokines or T-cell response). In some preferred embodiments, the variant has one or a limited number of amino acid substitutions (e.g., conservative or non-conservative substitutions), additions, or deletions (e.g., truncations) compared to wild type enzyme.

As used herein, the term "interest site" when used in reference to a ribonuclease refers to a region, subregion, and/or amino acid residue within the ribonuclease (e.g., human ribonuclease) that is modified or targeted for modification (e.g., for deletion, substitution or other type of mutation to create a ribonuclease variant). Accordingly, an "interest site" may be characterized as a "high interest site," a "medium interest site," or a "low interest site" based on characteristics of the ribonuclease described herein (e.g., biologic activity (e.g., ribonucleolytic activity, cancer cell killing activity, oligomerization capacity, etc.)) desired to be retained within the ribonuclease after modification of the same (e.g., for deletion, substitution or other type of mutation to create a ribonuclease variant, etc.). For example, sites that may be of interest are depicted in FIG. 15. The level of interest in modification of the residues in the ribonucleases is indicated by the use of the following symbols: low interest site ("−"), medium interest site ("0"), and high interest site ("+"). In addition, secondary structure is noted: where "a" or "a#"=alpha helix; "b" or "b#"=beta sheet. Contemplated sites of the ribonuclease that bind to substrate RNA are also labeled: "B1" and "B2"=substrate (base) binding site, "P1"=main active site, and "P2" and "P-1"=substrate (phosphate) binding sites. Cysteine residues involved in a disulfide bond are labeled by "disulf." Contact points that have been identified for the ribonuclease inhibitor are labeled with "RI". For angiogenin, the putative receptor binding site is labeled as "Rec."

The term "heterologous nucleic acid sequence" or "heterologous gene" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance or therapeutic benefits), etc.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes subjects who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

"Amino acid sequence" and terms such as "polypeptide" or "protein" are not meant to limit the amino acid sequence to the complete, native amino acid sequence associated with the recited protein molecule.

The terms "test compound" and "candidate compound" refer to any chemical or biological entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

The term "gene" refers to a nucleic acid (e.g., DNA) sequence that comprises coding sequences necessary for the production of a polypeptide or precursor (e.g., ribonucleases or ribonuclease conjugates of the present invention). The polypeptide can be encoded by a full length coding sequence or by any portion of the coding sequence so long as the desired activity or functional properties (e.g., enzymatic activity, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. Wild-type protein may be produced by synthetic methods. Wild-type proteins include, but are not limited to, forms that include post-translational modifications such as glycosylation as well as any preprocessed forms. In contrast, the terms "modified", "mutant", and "variant" refer to a gene or gene product that displays modifications in sequence when compared to the wild-type gene or gene product. It is noted that naturally-occurring mutants can be isolated; these are identified by the fact that they have altered nucleic acid or polypeptide sequence when compared to the wild-type gene or gene product. This is in contrast to synthetic mutants that are changes made in a sequence through human (or machine) intervention.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates. In some embodiments, fragments posses an activity of the native protein.

As used herein, the term "purified" or "to purify" refers to the removal of impurities and contaminants from a sample. For example, antibodies are purified by removal of non-immunoglobulin proteins; they are also purified by the removal of immunoglobulin that does not bind an intended target molecule. The removal of non-immunoglobulin proteins and/or the removal of immunoglobulins that do not bind an intended target molecule results in an increase in the percent of target-reactive immunoglobulins in the sample. In another example, recombinant polypeptides are expressed in host cells and the polypeptides are purified by the removal of host cell proteins; the percent of recombinant polypeptides is thereby increased in the sample.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

DETAILED DESCRIPTION OF THE INVENTION

In some embodiments, the present invention provides human ribonuclease (RNase 1) proteins that are used to treat or cure diseases, particularly cancer and viral infections. The compositions also find use in diagnostic applications (e.g., associated with drug screening or cancer characterization) and research applications. RNase 1 can be used as stand alone reagent or incorporated into general or specific delivery systems such as polymers, dendrimers, liposomes, polymeric nanoparticles, or block copolymer micelles. RNase 1 may also be co-administered with other drugs and compounds. A variety of human RNases are now known (e.g., Zhang et al., Nucleic Acids Research, 31:602 (2003); Zhang et al., Nucleic Acids Research, 30:1169 (2002), herein incorporated by reference in their entireties).

Previous experiments (See Cancer Res., 64:4870 [2004]) did not demonstrate a reduction in tumor volume with administration of human RNase 1 (human pancreatic RNase). In contrast, the present invention demonstrates that human RNase 1 and variants having similar activities and properties are effective in reducing tumor volume in animals.

In some embodiments, it is contemplated that RNase 1 is able to make chemotherapy or radiation resistant cells susceptible to standard or lower levels of treatment so that lower doses are effective and side effects reduced. In addition, RNase 1 is contemplated to provide benefit when used in combination with radiotherapy or other interventions, including but not limited to antibodies, small molecules, or gene therapy.

In some embodiments, the compositions and methods of the present invention are used to treat diseased cells, tissues, organs, or pathological conditions and/or disease states in a subject organism (e.g., a mammalian subject including, but not limited to, humans and veterinary animals), or in in vitro and/or ex vivo cells, tissues, and organs. In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the RNases of the present invention target cancer stem cells.

In some embodiments, the present invention contemplates the use of wild type human RNase 1. Wild type human RNase 1 include all forms of the enzyme including, but not limited to, polypeptides having the amino acid sequence of wild type RNase 1 encoded by nucleic acids of different sequences, as well as glycosylated, lipidated, and other modifications including covalent and non-covalent modifications.

The present invention further contemplates variants of wild type human RNase 1 (e.g., SEQ ID NO:1). A modified peptide can be produced in which the nucleotide sequence encoding the polypeptide has been altered, such as by substitution, deletion, addition (e.g., insertion), modifications (e.g., addition of additional molecules such as polyethylene glycol (PEG)) or post translational modifications (e.g., glycosylation). In some embodiments, insertions are insertions of large peptide segments (e.g., targeting proteins). Insertions have been made into proteins to incorporate additional functionality, such as recognition sequences (e.g., Characterization of an Adenovirus Vector Containing a Heterologous Peptide Epitope in the HI Loop of the Fiber Knob, J. Virology, 1998, 72, 1844). Additionally, the insertion may replace certain amino acids within the protein. The amino acids to be replaced may be selected to be similar in nature to sequences where insertions of amino acids can be placed, including unstructured or loop regions (e.g., Transplantation of a 17-amino acid a-helical DNA-binding domain into an antibody molecule confers sequence-dependent DNA recognition, PNAS, 1995, 92, 5214). The insertion may be another copy of the ribonuclease protein, either inserted at one of the termini or into the length of the first sequence. In other embodiments, variant RNase 1 of the present invention comprises a modified amino acid. In particularly preferred embodiments, these modifications do not significantly reduce the enzymatic activity or other desired activity or property of the modified human RNase 1. In other words, construct "X" can be evaluated in order to determine whether it is a member of the genus of modified or variant RNase 1 of the present invention as defined functionally.

Preferred variants maintain at least 1%, at least 5%, at least 15%, at least 30%, at least 50%, preferably at least 60%, even more preferably at least 75%, still more preferably at least 85%, yet more preferably at least 95% and most preferably at least 99% of the activity of wild type human ribonuclease 1. In some embodiments, the activity is enzymatic (e.g., degradation of RNA) activity. In other embodiments, activity is killing of cells (e.g., cancer cells). In other embodiments, preferred variants have similar properties as the wild type human RNase 1. For example, exemplary preferred properties include, but are not limited to, the speed of protein folding and ease of manufacturability, and low immunogenicity or toxicity in animals or lack of weight loss in animals administered the RNase 1. It should be noted that, in some embodiments, one of the activities or properties is rendered less desirable, but another is rendered desirable, such that, overall, the enzyme is useful (e.g., increased toxicity is traded for greater efficacy or vice versa).

In preferred embodiments, expression of RNase 1 or variants (e.g., recombinant expression) is greater than 50, and preferably greater than 75 mg/L. RNase 1 may be expressed in any suitable expression system. Bacterial and eukaryotic expression systems are available for production of recombinant proteins. In preferred embodiments, proteins are expressed at high levels to aid in purification and to obtain large quantities of protein for animal studies, clinical studies, or therapeutic manufacture and sale. In some embodiments, heterologous RNase 1 is expressed in vivo (e.g., via transfected nucleic acid constructs provided by transplantation of engineered ex vivo cells, gene therapy, generation of transgenic animals, etc.).

Preferred RNase 1 and variants thereof of the present invention exhibit tumor size reduction activity in animals. The present invention is not limited to a particular mechanism. Indeed, an understanding of the mechanism is not necessary to practice the present invention. Nonetheless, it is contemplated that one or more of several factors contribute to the activity of RNase 1 enzymes including, but not limited to, charge of the protein, pore forming ability, angiogenic effects, proper dosing considerations, etc.

Moreover, as described above, variant forms of human RNase 1 are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of human RNase 1 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (including, but not limited to, FADE (Mitchell et al., (2004). Molec. Simul. 30, 97-106); MAPS (Ban et al., Proceedings of the 8th Annual International Conference on Research in Computational Molecular Biology, 2004, 205-212), SYBYL (Tripos, Inc, St. Louis, Mo.); and PyMOL (available on the Internet web sit of sourceforge)).

Crystal structures of RNase 1 are described, for example in Pous et al. (Acta Crystallogr D Biol Crystallogr. 2001; 57, 498-505) and Pous et al. (J Mol Biol. 2000; 303, 49-60) and serve as the basis for selection of changes. In addition, crystal structures are available for other human pancreatic ribonucleases, including eosinophil derived neurotoxin (EDN, RNase 2; Swaminathan et al, Biochemistry, 2002, 41, 3341-3352, Mosimann et al J. Mol. Biol., 1996, 260, 540-552; Iyer et al J Mol Biol, 2005, 347, 637-655), eosinophil cationic protein (ECP, RNase 3; Mohan et al Biochemistry 2002; 41, 12100-12106; Boix et al Biochemistry, 1999, 38, 16794-16801; Mallorqui-Fernandez et al J. Mol. Biol, 2000, 300, 1297-1307), RNase 4 (Terzyan et al, 1999, 285, 205-214.) and angiogenin (RNase 5; Leonidas et al J. Mol. Biol. 1999, 285, 1209-1233; Leonidas et al Protein Sci., 2001, 10, 1669-1676; Papageorgiou et al EMBO J., 1997, 16, 5162-5177; Shapiro et al J. Mol. Biol., 2000, 302, 497-519.).

The amino acid sequences for additional ribonuclease gene family members have been determined, including RNase 6 (Rosenberg, et al, Nucleic Acids Research, 1996, 24, 3507-3513), RNase 7 (Harder et al, J. Biol. Chem., 2002, 277, 46779-46784), and RNase 8 (Zhang et al, Nucleic Acids Research, 2002, 30, 1169-1175.).

Variants may be produced by methods such as directed evolution or other techniques for producing combinatorial libraries of variants, described in more detail below. In still other embodiments of the present invention, the nucleotide sequences of the present invention may be engineered in order to alter a human RNase 1 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.). In some embodiments, changes are made in the nucleic acid sequence encoding a polypeptide of the present invention in order to optimize codon usage to the organism that the gene is expressed in.

Exemplary variants are described below, including, but not limited to, substitutions, truncations, chimeras, etc. The present invention is not limited to these particular variants. Both variants in the active site and substrate-binding region and away from the active site are contemplated to be within the scope of the present invention. Variants may be selected based on, for example, experimental data, computer modeling, and by rational design by comparison to other ribonucleases. Activities may be tested using assay to select the variants with the desired properties (see e.g., Raines et al., J. Biol. Chem, 273, 34134 (1998); Fisher et al., Biochemistry 37:12121 (1998); Guar et al., J. Biol. Chem., 276:24978 (2001); Bosch, et al., Biochemistry, 43:2167 (2004); Lin, J. Biol. Chem., 245:6726 (1970); Bal et al, Eur. J. Biochem., 245:465 (1997); Guar et al., Mol. Cell. Biochem., 275:95 (2005); Benito et al., Protein Eng., 15:887 (2002); Ribo et al., Biol. Chem. Hoppe-seyler, 375:357 (1994); DiGaetano et al., Biochem. J., 358:241 (2001); Trautwein et al., FEBS Lett., 281:277 (1991); Curran et al., Biochemistry 32:2307 (1993); Sorrentino et al., Biochemistry 42:10182 (2003); herein incorporated by reference in their entireties).

Figure 5:
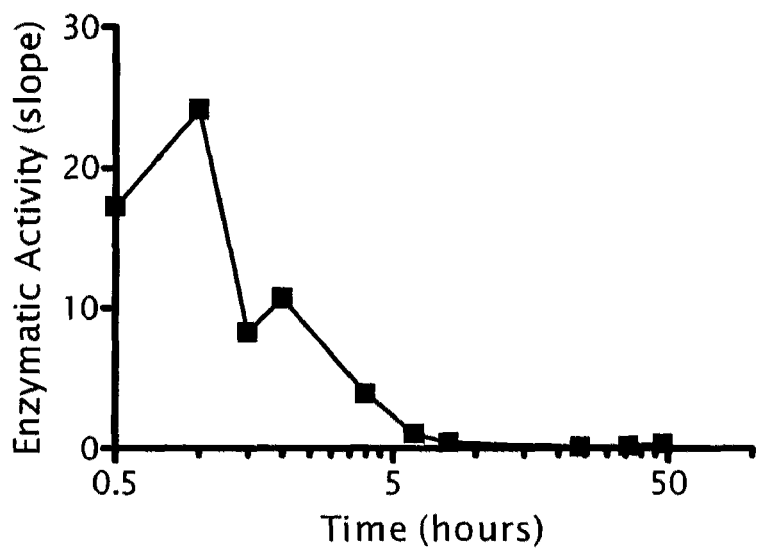
FIG. 5 shows pharmacokinetics of RNases in some embodiments of the present invention.

Exemplary amino acid locations for modification in the production of variants are provided in FIG. 15. One or more sites may be modified, as desired. Amino acid residues for human ribonucleases are provided in FIG. 5. The present invention provides a ranking of the utility for modification of each amino acid (e.g., as represented by interest in modifying (e.g., so as to result in a functional ribonuclease (e.g., comprising a desired property (e.g., cancer cell killing and/or ribonucleolytic activity). The amino acids are labeled in FIG. 15 as follows:

a low interest (−), medium interest (0), or high interest (+).

It will be appreciated that one or more modification sites may be used. Preferably, the selected sites are high interest sites. However, one or more medium interest or low interest sites may be used as desired and appropriate for the intended application. It should be noted that, in some embodiments, human RNase is produced (e.g., in vitro, in vivo or ex vivo) in such a way that a methionine (e.g., that is not part of wild type human RNase) is incorporated as the first amino acid of the protein (e.g., via the methods used to produce the protein (e.g., recombinant human ribonuclease (e.g., produced in *E. coli*))). Thus, in some embodiments, the numbering of amino acid residues depicted in FIG. 15 may be off by a numerical value of one (e.g., if a methionine is incorporated into the protein, then the numbering of the amino acid residues of the human RNases shown in FIG. 15 is off by 1 (i.e., because a methionine is incorporated in position 1, the numbering of the amino acids depicted in FIG. 15 will be short by one, e.g., the residue number 10 would actually be residue number 11 because of the methionine incorporated at position 1)). Similarly, the positions depicted in FIG. 15 may also be applied to corresponding numerical positions other related ribonucleases.

In some embodiments, the desired residues for modification (e.g., deletion, mutation, etc.) in human ribonucleases (e.g., hRNase 1) are selected to avoid disruption of the tertiary structure and/or stability of the ribonuclease. In some embodiments, these residues are on the surface of the protein (e.g., residues generally exposed to solvent (e.g., water or buffer)). For example, in some embodiments, the types of residues that are modified include, but are not limited to, amino acids that appear disordered in crystal structures, residues that contact the ribonuclease inhibitor protein, and amino acids not involved in tertiary structures (e.g., alpha helices and beta sheets), amino acids in loop regions between structures (e.g. alpha helices and beta sheets) as well as amino acids towards the end of the protein (the N- and C-termini). In some embodiments, additional amino acid residues are added to either the N- or C-terminus (e.g., to generate a RNase analogue and/or for conjugation of a water-soluble polymer).

Experiments conducted during the development of the present invention involved the formation of multiple variants of the human RNase 1. Such variants include changes of residues that have been described as binding sites for single and/or double stranded RNA. The enzymatic activity of these variants is provided below. Despite the range in enzymatic activity displayed by each RNase 1 variant, they were all active in xenograft models of non-small cell lung cancer. Thus, in addition to change made outside of the region attributed to enzyme activity, change may also be made in the region.

TABLE 1

| RNase | Enzymatic Activity (kcat/Km; M−1 s−1) |
|---|---|
| Wild type human RNase 1 | $2.97 \times 10^7$ |
| L86E/N88R/G89D/R91D RNase 1 | $1.17 \times 10^7$ |
| G38R/R39D/L86E/N88R/G89D/R91D RNase 1 | $4.90 \times 10^6$ |
| R4C/G38R/R39D/L86E/N88R/G89D/R91D/V118C RNase 1 | $1.28 \times 10^5$ |
| R4C/K7A/G38R/R39D/L86E/N88R/G89D/R91D/V118C RNase 1 | $1.69 \; 10^4$ |

The G38R/R39D/L86E/N88R/G89D/R91D RNase 1 and L86E/N88R/G89D/R91D RNase 1 displayed tumor growth inhibition in this model. Results are shown in FIG. 1 and Table 2.

TABLE 2

| | (% TGI) | | | | |
|---|---|---|---|---|---|
| | Starting volume | Final volume | (Final − start) | (Final − start)/Control | % TGI |
| Vehicle | 73 | 975 | 902 | 1 | 0 |
| L86E/N88R/G89D/R91D RNase 1 | 84 | 624 | 540 | 0.60 | 40 |
| G38R/R39D/L86E/N88R/G89D/R91D RNase 1 | 76 | 723 | 647 | 0.72 | 28 |
| cisplatin | 79 | 369 | 290 | 0.32 | 68 |

Figure 2:
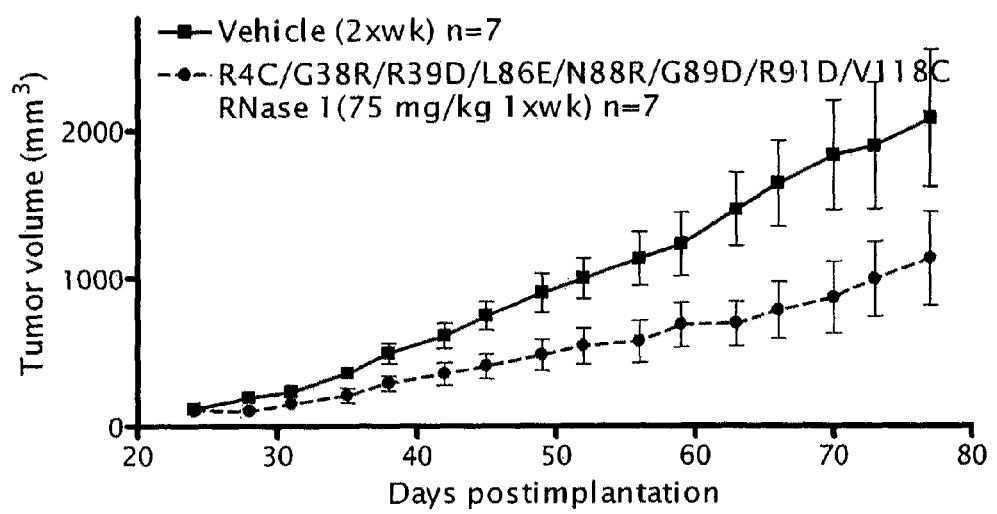
FIG. 2 shows in vivo activity of RNases in some embodiments of the present invention.
Figure 2:
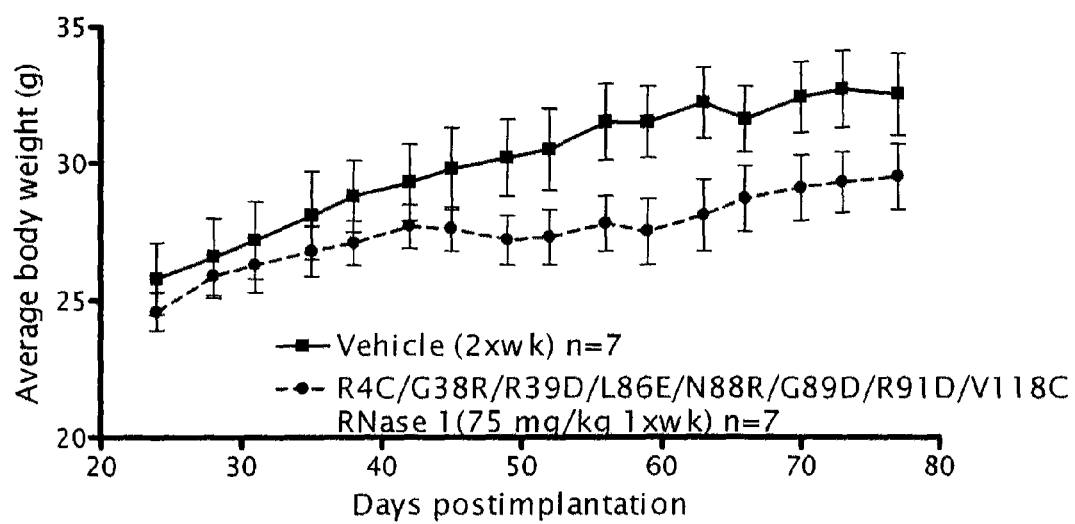

The R4C/G38R/R39D/L86E/N88R/G89D/R91D/V118C RNase 1 variant impacted tumor growth in the xenograft model. Results are shown in FIG. 2 and Table 3.

TABLE 3

| | (% TGI) | | | | |
|---|---|---|---|---|---|
| | Starting volume | Final volume | (Final − start) | (Final − start)/Control | % TGI |
| Vehicle | 118 | 2071 | 1953 | 1 | 0 |
| R4C/G38R/R39D/L86E/N88R/G89D/R91D/V118C RNase 1 | 108 | 1130 | 1022 | 0.52 | 48 |

Figure 3:
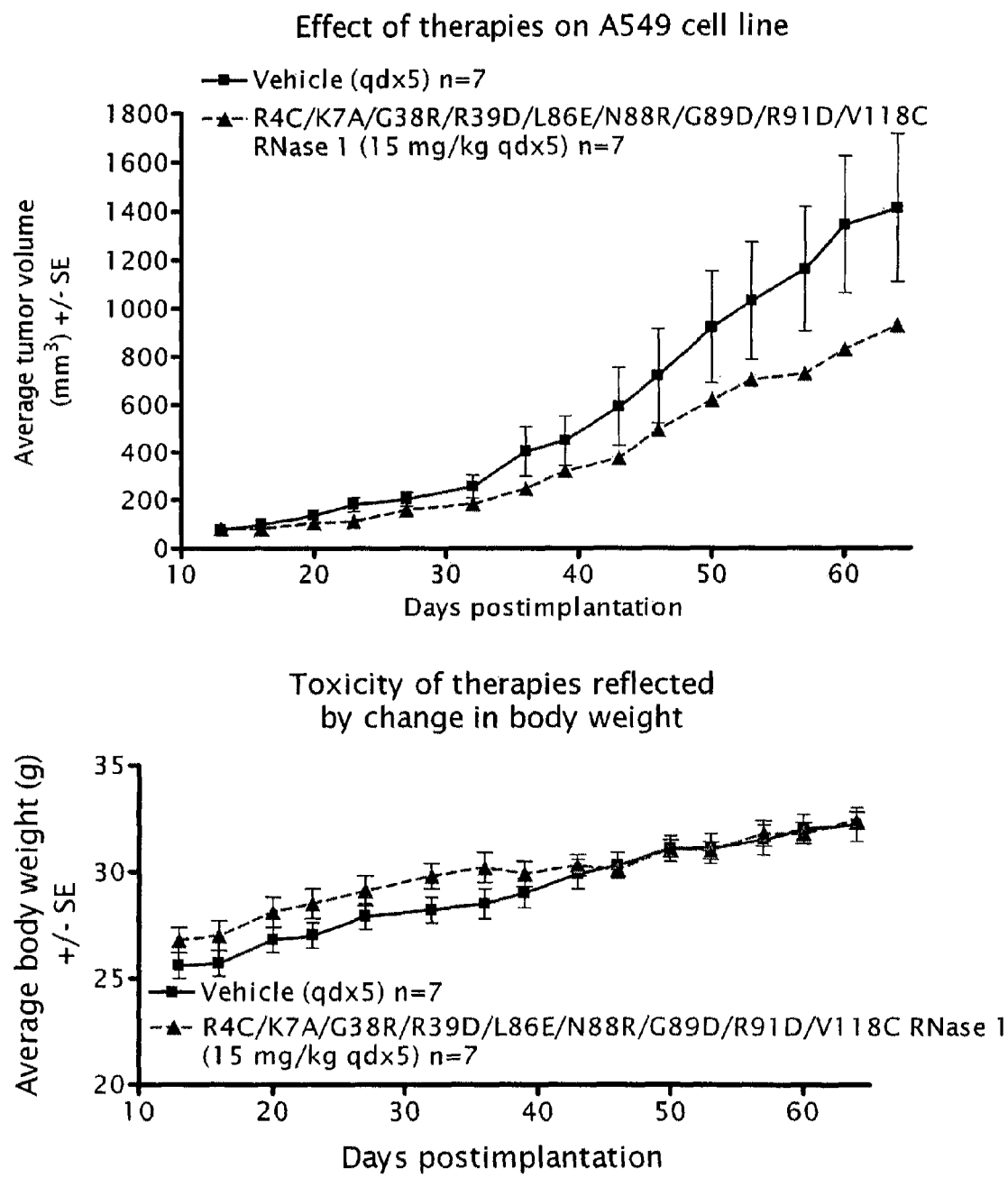
FIG. 3 shows in vivo activity of RNases in some embodiments of the present invention.

Despite having significantly lower enzymatic activity than the wild type RNase 1, the R4C/K7A/G38R/R39D/L86E/N88R/G89D/R91D/V118C RNase 1 variant demonstrated measurable tumor growth inhibition. Results are shown in FIG. 3 and Table 4.

TABLE 4

| | (% TGI) | | | | |
|---|---|---|---|---|---|
| | Starting volume | Final volume | (Final − start) | (Final − start)/Control | % TGI |
| Vehicle | 75 | 1407 | 1332 | 1 | 0 |
| R4C/K7A/G38R/R39D/L86E/N88R/G89D/R91D/V118C RNase 1 | 74 | 552 | 478 | 0.36 | 36 |

Thus, the present invention provides a broad array of ribonucleases that find use in the methods and compositions of the invention. Indeed, the examples above provide variants in the substrate and active sites that might have been expected to interfere with desired activities and properties of the protein. However, empirical data demonstrated that these variants substantially retain desired activities and properties of wild-type RNase 1.

In some embodiments, RNase 1 or a variant thereof is delivered to a target cell using complementation. For example, in some embodiments, two or more fragments of RNase 1 are delivered separately to a cell. The fragments re-associate to form a functional enzyme. In some embodiments, two protein fragments are delivered. In other embodiments, vectors comprising nucleic acids encoding fragments of RNase 1 are introduced into a cell or organism separately.

Suitable fragments for delivery by complementation may be determined by screening fragments (e.g., in a cell culture assay) for activity. Preferred fragments are those that rapidly re-associate to form a functional enzyme. Enzyme activity can be determined using any suitable method, including, but not limited to, those disclosed herein.

In some embodiments, the present invention utilizes digestion of RNases to produce S-peptide and S-protein (See, e.g., Hamachi et al., Bioorg Med Chem Lett 9, 1215-1218 (1999); Goldberg and Baldwin, Proc Natl Acad Sci, 96, 2019-2024 (1999); Asai et al., J Immun Meth, 299, 63-76 (2005); Backer et al., J Cont Release, 89, 499-511 (2003); Backer et al., Bioconj Chem, 15, 1021-1029 (2004)). For example, digestion of bovine RNase A by subtilisin results primarily in two fragments due to cleavage between Ala20 and Ser21. The shorter fragment (amino acids 1-20) is referred to as S-peptide, whereas the longer fragment (amino acids 20-124) is referred to as S-protein. The two fragments bind tightly at neutral pH and are sometime referred to as RNase S or RNase S'. RNase S is an active ribonuclease. The S-peptide-5-protein interaction has been used for affinity purification as well as in tertiary docking systems to target imaging agents or drugs. Thus, in some embodiments, the present invention provides S-peptide-5-protein for human ribonucleases.

In some embodiments, the present invention provides a composition comprising a plurality of human RNases (e.g., hRNase1). In some embodiments, the plurality of RNases comprise monomers, dimers, trimers, and/or higher order complexes (i.e., oligomers) of hRNases.

Combination Therapies

In some preferred embodiments, the RNase 1 or RNase 1 variants of the present invention are co-administered with other medical interventions, either simultaneously or sequentially. For example, for cancer therapy, any oncolytic agent that is routinely used in a cancer therapy may be co-administered with the compositions and methods of the present invention. For example, the U.S. Food and Drug Administration maintains a formulary of oncolytic agents approved for use in the United States. International counterpart agencies to the U.S.F.D.A. maintain similar formularies. Table 5 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents. It is contemplated, that in some cases, co-administration with the compositions of the present invention permits lower doses of such compounds, thereby reducing toxicity.

TABLE 5

| | | |
|---|---|---|
| Aldesleukin (des-alanyl-1, serine-125 human interleukin-2) | PROLEUKIN | Chiron Corp., Emeryville, CA |
| Alemtuzumab (IgG1κ anti CD52 antibody) | CAMPATH | Millennium and ILEX Partners, LP, Cambridge, MA |
| Alitretinoin (9-cis-retinoic acid) | PANRETIN | Ligand Pharmaceuticals, Inc., San Diego CA |
| Allopurinol (1,5-dihydro-4 H-pyrazolo[3,4-d]pyrimidin-4-one monosodium salt) | ZYLOPRIM | GlaxoSmithKline, Research Triangle Park, NC |
| Altretamine (N,N,N',N',N'',N''-hexamethyl-1,3,5-triazine-2,4,6-triamine) | HEXALEN | US Bioscience, West Conshohocken, PA |
| Amifostine (ethanethiol, 2-[(3-aminopropyl)amino]-, dihydrogen phosphate (ester)) | ETHYOL | US Bioscience |
| Anastrozole (1,3-Benzenediacetonitrile,a,a,a',a'-tetramethyl-5-(1H-1,2,4-triazol-1-ylmethyl)) | ARIMIDEX | AstraZeneca Pharmaceuticals, LP, Wilmington, DE |
| Arsenic trioxide | TRISENOX | Cell Therapeutic, Inc., Seattle, WA |
| Asparaginase (L-asparagine amidohydrolase, type EC-2) | ELSPAR | Merck & Co., Inc., Whitehouse Station, NJ |
| BCG Live (lyophilized preparation of an attenuated strain of *Mycobacterium bovis* (*BacillusCalmette-Gukin* [BCG], substrain Montreal) | TICE BCG | Organon Teknika, Corp., Durham, NC |
| Bevacizumab | AVASTIN | Genentech |
| bexarotene capsules (4-[1-(5,6,7,8-tetrahydro-3,5,5,8,8-pentamethyl-2-napthalenyl) ethenyl] benzoic acid) | TARGRETIN | Ligand Pharmaceuticals |
| bexarotene gel | TARGRETIN | Ligand Pharmaceuticals |
| Bleomycin (cytotoxic glycopeptide antibiotics produced by *Streptomyces verticillus*; bleomycin $A_2$ and bleomycin $B_2$) | BLENOXANE | Bristol-Myers Squibb Co., NY, NY |
| Capecitabine (5'-deoxy-5-fluoro-N-[(pentyloxy)carbonyl]-cytidine) | XELODA | Roche |
| Carboplatin (platinum, diammine [1,1-cyclobutanedicarboxylato(2-)-0,0']-, (SP-4-2)) | PARAPLATIN | Bristol-Myers Squibb |
| Carmustine (1,3-bis(2-chloroethyl)-1-nitrosourea) | BCNU, BICNU | Bristol-Myers Squibb |
| Carmustine with Polifeprosan 20 Implant | GLIADEL WAFER | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | CELEBREX | Searle Pharmaceuticals, England |
| Cetuximab | ERBITUX | ImClone/BMS |
| Chlorambucil (4-[bis(2chlorethyl)amino]benzenebutanoic acid) | LEUKERAN | GlaxoSmithKline |
| Cisplatin ($PtCl_2H_6N_2$) | PLATINOL | Bristol-Myers Squibb |
| Cladribine (2-chloro-2'-deoxy-b-D-adenosine) | LEUSTATIN, 2-CDA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | CYTOXAN, NEOSAR | Bristol-Myers Squibb |
| Cytarabine (1-b-D-Arabinofuranosylcytosine, $C_9H_{13}N_3O_5$) | CYTOSAR-U | Pharmacia & Upjohn Company |
| cytarabine liposomal | DEPOCYT | Skye Pharmaceuticals, Inc., San Diego, CA |
| Dacarbazine (5-(3,3-dimethyl-1-triazeno)-imidazole-4-carboxamide (DTIC)) | DTIC-DOME | Bayer AG, Leverkusen, Germany |
| Dactinomycin, actinomycin D (actinomycin produced by *Streptomyces parvullus*, $C_{62}H_{86}N_{12}O_{16}$) | COSMEGEN | Merck |

TABLE 5-continued

| | | |
|---|---|---|
| Darbepoetin alfa (recombinant peptide) | ARANESP | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DANUOXOME | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | CERUBIDINE | Wyeth Ayerst, Madison, NJ |
| Denileukin diftitox (recombinant peptide) | ONTAK | Seragen, Inc., Hopkinton, MA |
| Dexrazoxane ((S)-4,4'-(1-methyl-1,2-ethanediyl)bis-2,6-piperazinedione) | ZINECARD | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | TAXOTERE | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | ADRIAMYCIN, RUBEX | Pharmacia & Upjohn Company |
| doxorubicin | ADRIAMYCIN PFS INTRAVENOUS INJECTION | Pharmacia & Upjohn Company |
| doxorubicin liposomal | DOXIL | Sequus Pharmaceuticals, Inc., Menlo park, CA |
| dromostanolone propionate (17b-Hydroxy-2a-methyl-5a-androstan-3-one propionate) | DROMOSTANOLONE | Eli Lilly & Company, Indianapolis, IN |
| Dromostanolone propionate | MASTERONE INJECTION | Syntex, Corp., Palo Alto, CA |
| Elliott's B Solution | ELLIOTT'S B SOLUTION | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | ELLENCE | Pharmacia & Upjohn Company |
| Epoetin alfa (recombinant peptide) | EPOGEN | Amgen, Inc |
| Erlotinib (N-(3-ethynylphenyl)-6,7-bis(2-methoxyethoxy)quinazolin-4-amine) | TARCEVA | Genentech/OSI |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | EMCYT | Pharmacia & Upjohn Company |
| Etoposide phosphate (4'-Demethyl-epipodophyllotoxin 9-[4,6-O-(R)-ethylidene-(beta)-D-glucopyranoside], 4'-(dihydrogen phosphate)) | ETOPOPHOS | Bristol-Myers Squibb |
| etoposide, VP-16 (4'-demethyl-epipodophyllotoxin 9-[4,6-0-(R)-ethylidene-(beta)-D-glucopyranoside]) | VEPESID | Bristol-Myers Squibb |
| Exemestane (6-methylenandrosta-1,4-diene-3,17-dione) | AROMASIN | Pharmacia & Upjohn Company |
| Filgrastim (r-metHuG-CSF) | NEUPOGEN | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | FLUDARA | Berlex Laboratories, Inc., Cedar Knolls, NJ |
| Fluorouracil, 5-FU (5-fluoro-2,4(1H,3H)-pyrimidinedione) | ADRUCIL | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | FASLODEX | IPR Pharmaceuticals, Guayama, Puerto Rico |
| Gefitinib (N-(3-chloro-4-fluoro-phenyl)-7-methoxy-6-(3-morpholin-4-ylpropoxy)quinazolin-4-amine) | IRESSA | AstraZeneca |
| Gemcitabine (2'-deoxy-2',2'-difluorocytidine monohydrochloride (b-isomer)) | GEMZAR | Eli Lilly |
| Gemtuzumab Ozogamicin (anti-CD33 hP67.6) | MYLOTARG | Wyeth Ayerst |

TABLE 5-continued

| Drug | Brand | Company |
|---|---|---|
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [C$_{59}$H$_{84}$N$_{18}$O$_{14}$•(C$_2$H$_4$O$_2$)$_x$ | ZOLADEX IMPLANT | AstraZeneca Pharmaceuticals |
| Hydroxyurea | HYDREA | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | ZEVALIN | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | IDAMYCIN | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | GLEEVEC | Novartis AG, Basel, Switzerland |
| Interferon alfa-2a (recombinant peptide) | ROFERON-A | Hoffmann-La Roche, Inc., Nutley, NJ |
| Interferon alfa-2b (recombinant peptide) | INTRON A (LYOPHILIZED BETASERON) | Schering AG, Berlin, Germany |
| Irinotecan HCl ((4S)-4,11-diethyl-4-hydroxy-9-[(4-piperi-dinopiperidino)carbonyloxy]-1H-pyrano[3', 4':6,7] indolizino[1,2-b] quinoline-3,14(4H,12H) dione hydrochloride trihydrate) | CAMPTOSAR | Pharmacia & Upjohn Company |
| Letrozole (4,4'-(1H-1,2,4-Triazol-1-ylmethylene) dibenzonitrile) | FEMARA | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | WELLCOVORIN, LEUCOVORIN | Immunex, Corp., Seattle, WA |
| Levamisole HCl ((−)-(S)-2,3,5,6-tetrahydro-6-phenylimidazo [2,1-b] thiazole monohydrochloride C$_{11}$H$_{12}$N$_2$S•HCl) | ERGAMISOL | Janssen Research Foundation, Titusville, NJ |
| Lomustine (1-(2-chloro-ethyl)-3-cyclohexyl-1-nitrosourea) | CEENU | Bristol-Myers Squibb |
| Meclorethamine, nitrogen mustard (2-chloro-N-(2-chloroethyl)-N-methylethanamine hydrochloride) | MUSTARGEN | Merck |
| Megestrol acetate 17α(acetyloxy)-6-methylpregna-4,6-diene-3,20-dione | MEGACE | Bristol-Myers Squibb |
| Melphalan, L-PAM (4-[bis(2-chloroethyl) amino]-L-phenylalanine) | ALKERAN | GlaxoSmithKline |
| Mercaptopurine, 6-MP (1,7-dihydro-6H-purine-6-thione monohydrate) | PURINETHOL | GlaxoSmithKline |
| Mesna (sodium 2-mercaptoethane sulfonate) | MESNEX | Asta Medica |
| Methotrexate (N-[4-[[(2,4-diamino-6-pteridinyl)methyl]methylamino]benzoyl]-L-glutamic acid) | METHOTREXATE | Lederle Laboratories |
| Methoxsalen (9-methoxy-7H-furo[3,2-g][1]-benzopyran-7-one) | UVADEX | Therakos, Inc., Way Exton, Pa |
| Mitomycin C | MUTAMYCIN | Bristol-Myers Squibb |
| mitomycin C | MITOZYTREX | SuperGen, Inc., Dublin, CA |
| Mitotane (1,1-dichloro-2-(o-chlorophenyl)-2-(p-chlorophenyl) ethane) | LYSODREN | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | NOVANTRONE | Immunex Corporation |
| Nandrolone phenpropionate | DURABOLIN-50 | Organon, Inc., West Orange, NJ |
| Nofetumomab | VERLUMA | Boehringer Ingelheim Pharma KG, Germany |
| Oprelvekin (1L-11) | NEUMEGA | Genetics Institute, Inc., Alexandria, VA |
| Oxaliplatin (cis-[(1R,2R)-1,2-cyclohexanediamine-N,N'] [oxalato(2-)-O,O'] platinum) | ELOXATIN | Sanofi Synthelabo, Inc., NY, NY |

TABLE 5-continued

| | | |
|---|---|---|
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | AREDIA | Novartis |
| Pegademase ((monomethoxypolyethylene glycol succinimidyl) 11-17-adenosine deaminase) | ADAGEN (PEGADEMASE BOVINE) | Enzon Pharmaceuticals, Inc., Bridgewater, NJ |
| Pegaspargase (monomethoxypolyethylene glycol succinimidyl L-asparaginase) | ONCASPAR | Enzon |
| Pegfilgrastim (covalent conjugate of recombinant methionyl human G-CSF (Filgrastim) and monomethoxypolyethylene glycol) | NEULASTA | Amgen, Inc |
| Pentostatin | NIPENT | Parke-Davis Pharmaceutical Co., Rockville, MD |
| Pipobroman | VERCYTE | Abbott Laboratories, Abbott Park, IL |
| Plicamycin, Mithramycin (antibiotic produced by Streptomycesplicatus) | MITHRACIN | Pfizer, Inc., NY, NY |
| Porfimer sodium | PHOTOFRIN | QLT Phototherapeutics, Inc., Vancouver, Canada |
| Procarbazine (N-isopropyl-μ-(2-methylhydrazino)-p-toluamide monohydrochloride) | MATULANE | Sigma Tau Pharmaceuticals, Inc., Gaithersburg, MD |
| Quinacrine (6-chloro-9-(1-methyl-4-diethyl-amine) butylamino-2-methoxyacridine) | ATABRINE | Abbott Labs |
| Rasburicase (recombinant peptide) | ELITEK | Sanofi-Synthelabo, Inc., |
| Rituximab (recombinant anti-CD20 antibody) | RITUXAN | Genentech, Inc., South San Francisco, CA |
| Sargramostim (recombinant peptide) | PROKINE | Immunex Corp |
| Sorafenib | NEXAVAR | Bayer/Onyx |
| Streptozocin (streptozocin 2-deoxy-2-[[(methylnitrosoamino)carbonyl]amino]-a(and b)-D-glucopyranose and 220 mg citric acid anhydrous) | ZANOSAR | Pharmacia & Upjohn Company |
| Sunitinib malate | SUTENT | Pfizer |
| Talc ($M_g3S_{14}O_{10}(OH)_2$) | SCLEROSOL | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | NOLVADEX | AstraZeneca Pharmaceuticals |
| Temozolomide (3,4-dihydro-3-methyl-4-oxoimidazo[5,1-d]-as-tetrazine-8-carboxamide) | TEMODAR | Schering |
| teniposide, VM-26 (4'-demethyl-epipodophyllotoxin 9-[4,6-0-(R)-2-thenylidene-(beta)-D-glucopyranoside]) | VUMON | Bristol-Myers Squibb |
| Testolactone (13-hydroxy-3-oxo-13,17-secoandrosta-1,4-dien-17-oic acid [dgr]-lactone) | TESLAC | Bristol-Myers Squibb |
| Thioguanine, 6-TG (2-amino-1,7-dihydro-6H-purine-6-thione) | THIOGUANINE | GlaxoSmithKline |
| Thiotepa (Aziridine,1,1',1''-phosphinothioylidynetris-, or Tris (1-aziridinyl) phosphine sulfide) | THIOPLEX | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | HYCAMTIN | GlaxoSmithKline |
| Toremifene (2-(p-[(Z)-4-chloro-1,2-diphenyl-1-butenyl]-phenoxy)-N,N-dimethylethylamine citrate (1:1)) | FARESTON | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | BEXXAR | Corixa Corp., Seattle, WA |
| Trastuzumab (recombinant monoclonal $IgG_1$ kappa anti-HER2 antibody) | HERCEPTIN | Genentech, Inc |

TABLE 5-continued

| | | |
|---|---|---|
| Tretinoin, ATRA (all-trans retinoic acid) | VESANOID | Roche |
| Uracil Mustard | URACIL MUSTARD CAPSULES | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | VALSTAR | Anthra --> Medeva |
| Vinblastine, Leurocristine ($C_{46}H_{56}N_4O_{10} \cdot H_2SO_4$) | VELBAN | Eli Lilly |
| Vincristine ($C_{46}H_{56}N_4O_{10} \cdot H_2SO_4$) | ONCOVIN | Eli Lilly |
| Vinorelbine (3',4'-didehydro-4'-deoxy-C'-norvincaleukoblastine [R-(R*,R*)-2,3-dihydroxybutanedioate (1:2)(salt)]) | NAVELBINE | GlaxoSmithKline |
| Zoledronate, Zoledronic acid ((1-Hydroxy-2-imidazol-1-yl-phosphonoethyl) phosphonic acid monohydrate) | ZOMETA | Novartis |

In other embodiments, the RNase 1 compositions of the present invention are used in combination with variant human RNase proteins (See e.g., U.S. patent application Ser. No. 11/105,041, herein incorporated by reference in its entirety) that are toxic to cells.

A current and still developing approach to cancer therapy involves using cancer cell-specific reagents to target a malignant tumor, although the proteins of the present invention may be used without targeting reagents. These toxic reagents can be produced by attaching a toxic payload to a cell-specific delivery vector. Over the past few years, a wide variety of tumor-specific targeting proteins, including antibodies, antibody fragments, and ligands for cell surface receptors have been developed and clinically tested. These targeting molecules have been conjugated to several classes of therapeutic toxins such as small molecule drugs, enzymes, radioisotopes, protein toxins, and other toxins for specific delivery to patients. While these efforts have made meaningful inroads to treat cancers, significant challenges lie ahead to develop more effective toxins, to create more robust and specific delivery systems, and to design therapeutic proteins and protein vectors that avoid a detrimental immune response in humans.

Ribonuclease (RNase) proteins have been tested as human therapeutics because they have some selectivity for tumor cells; this has been demonstrated most clearly with an RNase from *Rana pipiens* early embryos. *Rana pipiens* is a species of leopard frogs and its embryonic RNase is distantly related to the more highly conserved bovine and human pancreatic ribonucleases. In mammalian cells, pancreatic-type ribonucleases, such as RNase A, are secretory enzymes that catalyze the degradation of RNA to ribonucleotides and their activity is inhibited by binding to ribonuclease inhibitor (RI), a ubiquitous cytosolic protein. The present invention is not limited to a particular mechanism. Indeed, an understanding of the mechanism is not necessary to practice the present invention. Nonetheless, it is contemplated that ribonuclease inhibitor binds exceptionally tight to pancreatic-type RNases, abating their activity and thereby making them non-toxic to normal or cancer cells. If the RNase activity is inhibited, the cellular RNA is undamaged and the cell remains viable. In normal cells the ribonuclease activity is tightly controlled, but if ribonuclease activity is uncontrolled, the ribonucleolytic activity destroys cellular RNA and kills the cell. There are two main approaches to diminishing the binding of ribonucleases to the ribonuclease inhibitor protein. The first approach is to select a ribonuclease that is evolutionarily distant to humans and is not inhibited by human ribonuclease inhibitor protein.

The frog (*Rana pipiens*) ribonuclease, when placed in a human cell, is not strongly inhibited by RI and its RNase activity destroys cellular RNA and kills the target cell. This has been the approach with a specific *Rana pipiens* RNase called Ranpirnase. Ranpirnase is generic name of the pharmaceutical that is described and claimed in U.S. Pat. No. 5,559,212 and that is presently known by the registered trademark ONCONASE.

The second approach is to mutate mammalian ribonucleases so that they have diminished binding to the human ribonuclease inhibitor. These mutated enzymes provide high levels of ribonucleolytic activity within cancer cells because of disruption of binding to RI. This unregulated activity is particularly lethal to cancer cells. This mutation approach has been demonstrated with the mammalian proteins bovine RNase A and human RNase 1 and is described in U.S. Pat. Nos. 5,389,537 and 6,280,991, the disclosures of which are herein incorporated by reference in their entireties. Surprisingly, the present invention demonstrates that wild type human ribonuclease 1 and equivalent variants have the ability to kill cancer cells.

An ideal protein candidate for cancer therapy would be more toxic to tumor cells compared to non-cancerous cells and would be targetable to a specific tumor. This candidate should have few side effects and should not stimulate a detrimental human immune response. Therapeutic proteins that elicit detrimental immune responses in humans are often problematic and sometimes unacceptable. Experiments conducted during the course of development of the present invention demonstrated that human RNase 1 exhibited significant anti-tumor activity in mouse xenografts while exhibiting minimal toxicity. Accordingly, in some embodiments, the present invention provides RNase 1 proteins, alone or in combination with other therapeutic agents, for use in killing cancer cells or degrading toxic RNA.

Certain preferred embodiments of the present invention are described below. While the present invention is illustrated with human RNase 1 proteins, the present invention is not limited to the use of RNase 1 of human origin. The present invention contemplates the use of homologs of RNase 1 from any organism and engineered proteins.

Genetic Therapy

In some embodiments, RNase 1 or a variant thereof is provided as a nucleic acid encoding the RNase. Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

Therapeutic Antibodies and Delivery of Cytotoxins

Antibodies are glycoprotein molecules produced by white blood cells (B-lymphocytes) of the immune system and their function is to recognize and bind to matter harmful to the organism. Once an antigen is marked by an antibody, it is destroyed by other components of the immune system. A typical organism makes millions of different antibodies, each designed to bind a specific epitope (or antigenic determinant) on the foreign antigen. Antibodies naturally combine specificity (the ability to exquisitely discriminate diverse harmful molecules) and affinity (the ability to tightly lock onto those targets) with the ability to recruit effector functions of the immune system such as antibody- and complement-mediated cytolysis and antibody-dependent cell-mediated cytotoxicity (ADCC). Many new therapeutic approaches involving antibodies have succeeded in potentiating the natural antibody functions to treat or cure diseases.

Alternatively, a "toxic payload" (such as a radioactive element or a toxin) attached to the antibody can be accurately delivered to the pathogenic target. The following table lists the mechanisms of some cancer therapeutic antibodies, including three antibody conjugates that carry a toxic payload for lymphomas and leukemias. (Drug Discovery Today, Vol. 8, No. 11 June 2003). Two of the conjugates, ZEVALIN and BEXXAR, carry radioactive iodine as the toxin and the third, MYLOTARG, carries a cytotoxic antitumor antibiotic, calicheaminin which is isolated from a bacterial fermentation. The Mylotarg antibody binds specifically to the CD33 antigen which is expressed on the surface of leukemic blasts that are found in more than 80% of patients with acute myeloid leukemia (AML). The antibody in this conjugate has approximately 98.3% of its amino acid sequences derived from human origins.

TABLE 6

| Antibody Mode of Action | Product | Antibody Target |
| --- | --- | --- |
| Blockade Ligand binding | ERBITUX | EGF receptor |
|  | HUMAX-EGFR | EGF receptor |
| Complement Dependent Cytotoxicity | RITUXAN | CD20 |
|  | HUMAX-CD20 | CD20 |
|  | CAMPATH-1H | CD52 |
| Antibody dependent cell-mediated cytotoxicity | RIXTUXAN | CD20 |
|  | HUMAX-CD20 | CD20 |
|  | HERCEPTIN | Her-2/neu |
|  | HUMAX-EGFR | EGF receptor |
| Apoptosis induction | Various | IdiotypeB cell tumors |
| Disruption signaling | 2C4 (PERTUZUMAB) | Her-2/neu |
| Inhibition angiogenesis | AVASTIN | VEGF |
| Targeted radiolysis conjugate | ZEVALIN | CD20 |
|  | BEXXAR | CD20 |
| Toxin-mediated killing by conjugate | MYLOTARG | CD33 |
| Antagonist activity | MDX-010 | CTLA4 |
| Agonist activity | Various | CD40, CD137 |
| Antagonist activity | Preclinical MAb | Epithelial cell receptor protein tyrosine kinase (EphA2) |
| Antagonist activity | Phase II Mab | alpha 5 beta 3 integrin (receptor) |
| Antagonist activity | Phase I bispecific single chain monoclonal antibody | CD19/CD3 |
| Antagonist activity | Preclinical MAb | Interleukin 9 |
| Antagonist activity | RespiGam Polyclonal Antibody | Respiratory syncytial virus |
| Antagonist activity | Phase II MAb | CD2 |
| Catalytic Activity | Mab | Cocaine cleavage |
| Anti-infective, bacteria | Mab | bacteria |
| Immunosuppressive Agents | Mab | Graft versus Host Disease |
| Anti-infective, virus | Mab | Human metapneumovirus |
| Cytostatic agent | Mab | Platelet derived growth factor |

TABLE 6-continued

| Antibody Mode of Action | Product | Antibody Target |
|---|---|---|
| Cancer growth and metastosis | Preclinical MAb | Human beta hydroxylases |
| Treatment of autoimmune disease | MAb Medi 507 | Mixed lymphocyte responses |
| Anti-infective, virus | Polyclonal antibody | cytomegalovirus |
| Anti-idiotype antibody | Mab | Neu-glycolyl-GM3 ganglioside |
| Prodrug carrier | Mab | Immungen's CC 1065 prodrugs |
| Toxin-mediated killing by conjugate | Preclinical MAb and taxane derivatives | Various by Immunogen |
| Toxin-mediated killing by conjugate | Cantuzumab mertansine conjugate | Can Ag receptor by immunogen |
| Toxin-mediated killing by conjugate | Phase II MAb maytansinoid conjugate | CD56 |
| Toxin for mitosis inhibition | MAb maitansine conjugate | various |
| Toxin-mediated killing by conjugate | Preclinical MAb cytotoxic drug DM1 conjugate | Antigen on squamous cell cancer (Immunogen) |

Any of the targeting antibodies or agents used in these products may also be employed by the compositions and methods of the present invention.

Generally, the most specific method for targeting toxins is the use of monoclonal antibodies or antibody fragments that are designed to recognize surface antigens specific to tumor cells. Because normal cells lack the surface antigens, they are not targeted and killed by the toxin conjugate. Whole antibodies have two domains: a variable domain that gives the antibody its affinity and binding specificity and a constant domain that interacts with other portions of the immune system to stimulate immune responses in the host organism. The variable domain is composed of the complementarity determining regions (CDRs), which bind to the antibody's target, and a framework region that anchors the CDRs to the rest of the antibody and helps maintain CDR shape. The six CDR's in each antibody differ in length and sequence between different antibodies and are mainly responsible for the specificity (recognition) and affinity (binding) of the antibodies to their target markers.

The functions of antibodies are reflected in their characteristic three-dimensional structure, which is ultimately determined by the primary sequence of amino acids and how those amino acids fold into a functional 3-dimensional protein chain. A step in developing therapeutic monoclonal antibodies is to simultaneously optimize biochemical and cellular functions for anti-cancer performance and still keep the protein as humanlike as possible to minimize any anti-antibody human immune response.

Monoclonal antibodies were originally produced in mice, but when they are used in human therapeutic applications, they present formidable obstacles. Mouse antibodies are recognized as foreign by the human immune system and thus they provoke the Human Anti-Mouse Antibody or HAMA reaction. The HAMA reaction alters the mouse monoclonal effectiveness and can cause severe adverse symptoms in the recipient. Furthermore, mouse antibodies are simply not as effective as human antibodies in mediating the human immune system to destroy the malignant cells. For these reasons, it is often desired to design monoclonal antibodies that are as humanlike as possible but still maintain optimal biochemical, immunological, and therapeutic performance.

There are several factors that influence whether a therapeutic antibody will induce an immune response in the human host. These include the efficiency of uptake by an APC (antigen presenting cell) via pinocytosis, receptor-mediated endocytosis, or phagocytosis. The efficiency of uptake is in turn influenced by the route of administration, the solubility (or aggregation) of the protein, its receptor binding specificity, and whether the protein is recognized by class II major histocompatibility complex (MHC) molecules, T-cell receptors (TCR), and B-cell receptors (BCR). One of the most straightforward ways to evade the human immune response is to make the therapeutic protein sequence and structure as humanlike as possible.

Two main approaches have emerged to produce human or humanized therapeutic monoclonal antibodies, either used alone as a therapeutic or as a carrier for a toxin. These include 1) 'humanizing' mouse or other non-human antibodies to make them compatible with the human immune system and 2) producing fully human antibodies in transgenic mice or by using genetic engineering methods in the laboratory. The processes have produced several categories of monoclonal antibodies. These include mouse, chimaeric, humanized and human antibodies. They are described briefly below:

1. Murine Monoclonal antibodies from mice and rats: The original Kohler and Milstein technology from 1975 provided mouse monoclonal antibodies using a hybridoma technology. These have been used therapeutically. In 1986, the first approved use of mouse monoclonals was for transplant patients whose immune system was suppressed to avoid organ rejection. Rodent antibodies tend to provoke strong Human anti-Murine Antibody (HAMA) immune responses that restrict their usefulness for repeated application in the same patient.

2. Chimaeric Antibodies: These are mutated antibodies in which the entire variable regions of a functional mouse antibody are joined to human constant regions. These antibodies have human effector functions from the constant (Fc regions) such as activating complement and recruiting immune cells. These chimaeric antibodies also reduce the immunogenicity (HAMA) caused by the mouse constant region.

3. Humanized/CDR grafted/Reshaped antibodies. These antibodies are more humanlike than chimaeric antibodies because only the complementarity determining regions from the mouse antibody variable regions are combined with framework regions from human variable regions. Because these antibodies are more human-like than chimaeric antibodies, it is expected they could be designed to be less immunogenic when given to human in recurring therapeutic doses. Using computer modeling software to guide the humanization of murine antibodies or random shuffling of sequences followed by screening, it is possible to design an antibody that retains most or all of the binding affinity and specificity of the murine antibody but which is >90% human.
4. Human antibodies from immune donors: Some antibodies have been rescued from immune human donors using either Epstein Barr Virus transformation of B-cells or by PCR cloning and phage display. By definition these antibodies are completely human in origin.
5. Fully human antibodies from phage libraries: Synthetic phage libraries have been created which use randomized combinations of synthetic human antibody V-regions. By panning these libraries against a target antigen, these so called 'fully human antibodies' are assumed to be very human but possibly more diverse than natural antibodies.
6. Fully human antibodies from transgenic mice: Transgenic mice have been created that have functional human immunoglobulin germline genes sequences. These transgenic mice produce human-like antibodies when immunized.

The human antibodies produced by methods 4, 5, and 6 are typically most desired because they produce a starting antibody that contains no mouse or otherwise "foreign" protein sequences that should stimulate an immune response in human patient. This approach (in 4, 5, and 6) also can bypass the challenge of substituting mouse CDR regions into human frameworks that often alters the 3-dimensional structure of the variable region, thereby changing the antibody's binding and specificity. This approach (in 4, 5, 6) successfully produced an anti-CD3 antibody. The murine version elicited neutralizing antibodies after a single dose in all patients tested, while a humanized version was only immunogenic in 25% of patients following multiple injections.

Besides making monoclonal antibodies as human-like as possible in the primary sequence to escape the human immune response, several other approaches make antibodies less immunogenic and more therapeutically effective are available. One approach is to covalently modify the antibody surface with reagents such as polyethylene glycol (PEG) to suppress its antigenicity and improve its solubility. These biochemical modifications also can have several other benefits such as reduced toxicity, increased bioavailability, and improved efficacy. Another approach is to use antibody fragments in which the potentially antigenic parts of the mouse antibody, such as the constant region, have been removed. This approach typically works only when the regulatory components within the antibody constant region are not required for therapeutic efficacy. Neither of these approaches has proven completely satisfactory, which has driven the humanization effort to produce 'the ideal' antibody candidate mentioned above.

In addition to antibody delivery vectors, toxic molecules can be delivered to cancer cells using several other specific and non-specific vectors including peptides, polymers, dendrimers, liposomes, polymeric nanoparticles, and block copolymer micelles. For example, peptides that bind to the leutinizing hormone-releasing hormone have been used to target a small molecule toxin, camptothecin, to ovarian cancer cells (Journal of Controlled Release, 2003, 91, 61-73.).

Ribonucleases such as RNase 1 are effective toxins in human cells, particularly against cancer cells. The following references, each of which is herein incorporated by reference in its entirety, describe some chemical conjugates of ribonucleases to targeting proteins (including proteins and antibodies): Newton et al. (2001), Blood 97(2): 528-35, Hursey et al. (2002) Leuk Lymphoma 43(5): 953-9, Rybak et al., (1991) Journal of Biological Chemistry 266(31): 21202-7, Newton et al. (1992) Journal of Biological Chemistry 267(27): 19572-8, Jinno and Ueda (1996) Cancer Chemother Pharmacol 38: 303-308, Yamamura et al. (2002) Eur J Surg 168: 49-54, Jinno et al. (1996) Life Sci 58: 1901-1908, Suzuki et al. (1999) Nature Biotechnology 17(3): 265-70, Rybak et al. (1992), Cell Biophys 21(1-3): 121-38, Jinno et al. (2002) Anticancer Res. 22: 4141-4146.

Due to the minimal side effects seen thus far for human ribonuclease 1, the ribonuclease itself could be used to target drugs to diseased cells, such as cancer cells.

In particular, some embodiments of the present invention provide recombinant constructs comprising one or more of the sequences as broadly described above. In some embodiments of the present invention, the constructs comprise a vector, such as a plasmid or viral vector, into which a sequence of RNase 1 has been inserted, in a forward or reverse orientation. In still other embodiments, the heterologous structural sequence is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pet 22b, pet26b, pet 30b (Novagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline, kanamycin, or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome-binding site for translation initiation and a transcription terminator. In still other embodiments of the present invention, the vector may also include appropriate sequences for amplifying expression.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerivisiae, Schizosaccharomyces pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, transformation, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

The polypeptides of the present invention may also be chemically synthesized (Gutte, B. and Merrifield, R. B. The synthesis of ribonuclease A. J. Biol. Chem. 1971, 2461, 1722-1741.).

Pharmaceutical Compositions

The present invention further provides pharmaceutical compositions (e.g., comprising the cell killing compositions described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The preferred method of administration is by intravenous or IP injection. It is alternatively possible to use injection into the tumor to be treated. In some embodiments, administration is continued as an adjuvant treatment for an additional period (e.g., several days to several months).

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active pharmaceutical agents of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual pharmaceutical compositions, and can generally be estimated based on $EC_{50}s$ found to be effective in in vitro and in vivo animal models or based on the examples described herein. In general, dosage is from 0.01 μg to 100 g per kg of body weight, for example between 0.1 and 1000 mg per kg of body weight, preferably between 0.1 and 500 mg/kg of body weight, and still more preferably between 0.1 and 200 mg/kg of body weight, for a period of between 1 and 240 minutes (e.g., between 2 and 60 minutes and preferably between 15 and 45 minutes). Dosages may be administered as often as need to obtain the desired effect (e.g., reduction of tumor size or number of cancerous cells), for example once or more daily to once or more weekly or monthly. In some embodiments, the compositions are administered weekly at a dose of between 0.1 and 10 mg (e.g., 1 mg) for a period of between 5 and 60 minutes (e.g., 30 minutes). The treating physician can estimate repetition rates for dosing based on measured residence times and concentrations of the drug in bodily fluids or tissues. Following successful treatment, it may be desirable to have the subject undergo maintenance therapy to prevent the recurrence of the disease state once or more daily, to once every 20 years. In some preferred embodiments, dosages are 0.25-1000 mg/kg daily, weekly, or monthly to achieve the desired therapeutic effect. In some preferred embodiments, dosages are 50 mcg/m$^2$ to 400 mcg/m$^2$ daily, weekly, or monthly to achieve the desired therapeutic effect. Drugs are also sometimes dosed in units of activity per dose as opposed to amount (weight) of drug.

EXAMPLES

The following examples serve to illustrate certain preferred embodiments and aspects of the present invention and are not to be construed as limiting the scope thereof.

Example 1

Enzymatic Activity Assay

The enzymatic activity of the wild type human RNase 1 was determined using a fluorescent assay based on fluorescence resonance energy transfer (FRET). The substrate for the assay, 5'FAM-ArUAA-3'TAMRA (IDT), is not fluorescent until cleaved.

In a typical assay, the buffer (160 microliters of 100 mM NaCl, 100 mM Tris, pH 7.0, 100 microgram/mL BSA) is added to the wells of a 96-well non-binding surface, black, polystyrene plate. The RNase (typically 10 microliters of an approximately $2 \times 10^{-10}$ M solution) is also added. Substrate (30 microliters of a 1.33 micromolar solution of 5'FAM-ArUAA-3'TAMRA) is then added to each well, and the samples mixed. The plate is read on a fluorescent plate reader immediately.

Figure 4:
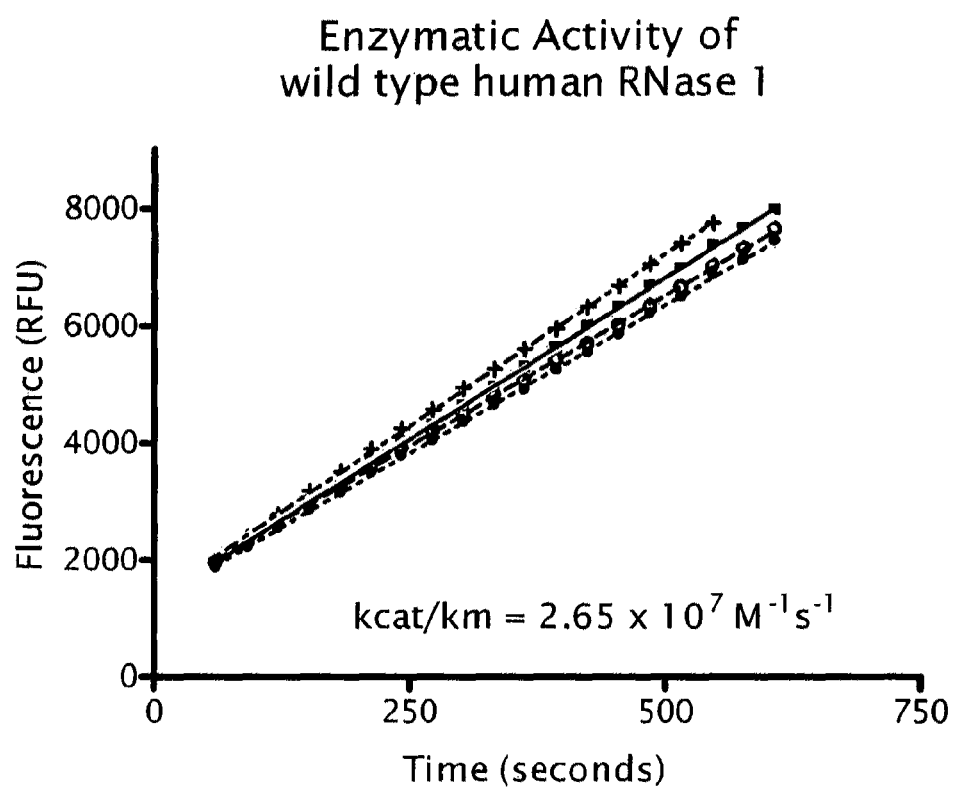
FIG. 4 shows enzyme activity of RNases in some embodiments of the present invention.

Control wells are included for F0 (no enzyme) and Fmax determinations (typically 10 microliters of a 0.1 mg/mL solution of RNase A per 200 microliter assay). In this example, wild type human RNase 1 had a $k_{cat}/K_M = 2.65 \times 10^7$ $M^{-1}$ $sec^{-1}$. The results are shown in FIG. 4.

Example 2

Pharmacokinetic Determination in BALB/c Mice

Sixteen CD-1 mice (5 weeks old, Harlan) were injected with 75 mg per kg of body weight of wild type human RNase 1. Blood was collected from three mice at each of the following time points: 0.5, 1.0, 1.5, 2, 4, 6, 8, 24, 36, 48 hours. The animals were rotated for bleeding, leaving as much time as possible between bleeding times. The blood was allowed to clot for several hours at 4° C. and spun in a microfuge at top speed for 10 minutes. The serum was then collected and stored at −20° C.

The serum samples for each timepoint were pooled and the serum diluted (1:10,000). The enzymatic activity assay described in the previous example was used to analyze the samples. The slope of the line for each time point was plotted and is provided FIG. 5.

Example 3

In vivo Determination of Inhibition of Tumor Growth

Cells from a non-small cell lung cancer cell line (A549) were grown in nine T175 flasks in F12K media and 10% fetal calf serum until the cells were confluent. $4.5 \times 10^6$ cells (in 100 microliters) were injected into the right rear flank of 4-5 week old male homozygous (nu/nu) nude mice (Harlan, Madison Wis.). Tumors were allowed to grow to an average size of ≧75 mm$^3$ before treatments were initiated. Animals of each tumor type, with the properly sized tumors, were divided into treatment groups, including one set of animals treated weekly with vehicle (phosphate buffered saline, PBS). The vehicle and the test agents were all administered by intraperitoneal injection. Each animal was weighed twice a week during treatment. The tumors were measured twice weekly using calipers. Tumor volume (mm³) was determined by using the formula for an ellipsoid sphere:

$$\text{volume} = \frac{l \times w^2}{2}$$

Figure 6:
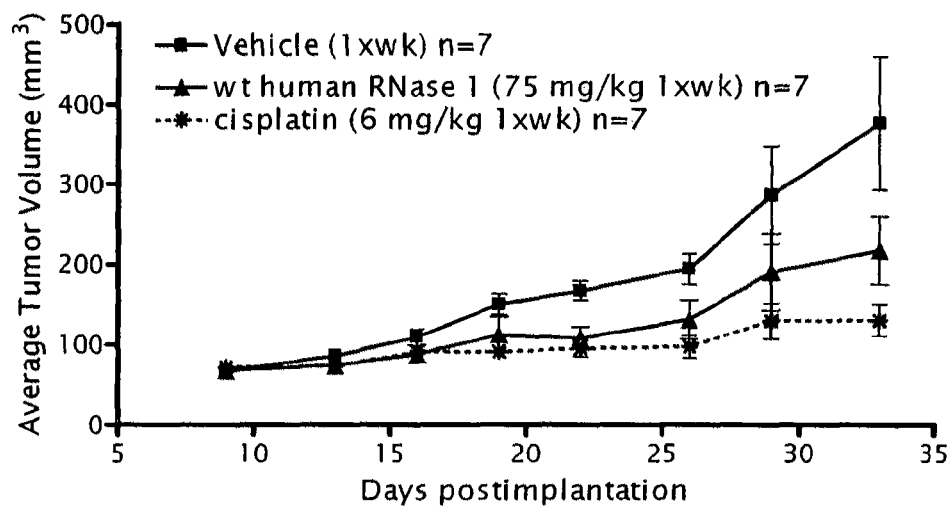
FIG. 6 shows in vivo activity of RNases in some embodiments of the present invention.
Figure 6:
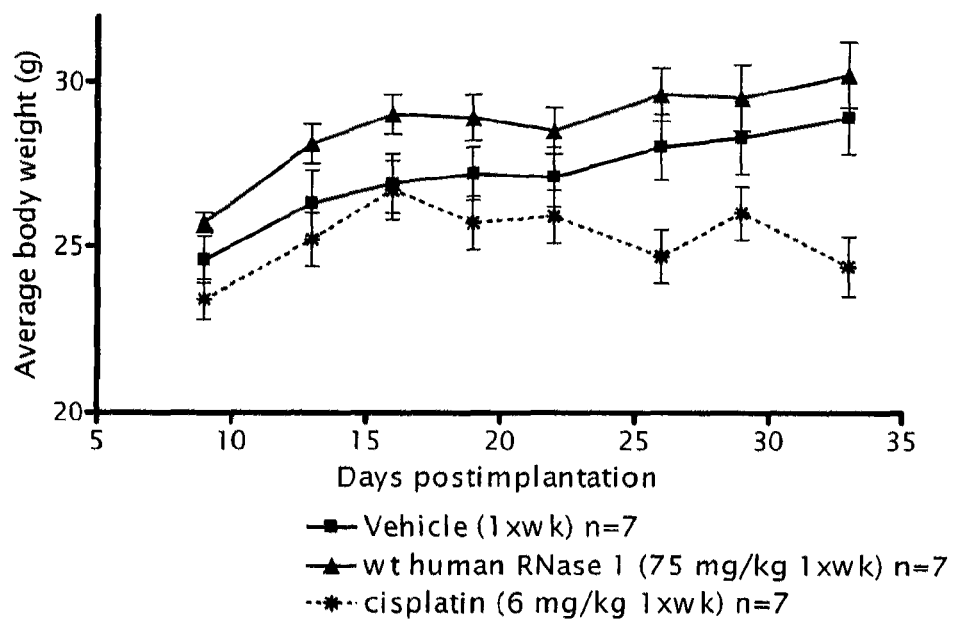

Results are shown in FIG. 6 and Table 7. The efficacy of wild type human RNase 1 is shown relative to cisplatin. The RNase 1 was administered at 75 mg per kg of body weight of the animal once a week (75 mg/kg 1×wk), while the cisplatin was used at 6 mg/kg once a week. The value of n represents the number of animals in the specific treatment arm of the experiment.

TABLE 7

|  | Starting volume | Final volume | (Final − start) | (Final − start)/ Control | % TGI |
|---|---|---|---|---|---|
| Vehicle | 67 | 376 | 309 | 1 | 0 |
| wt human RNase 1 (75 mg) | 68 | 217 | 149 | 0.49 | 51% |
| cisplatin (6 mg) | 72 | 130 | 58 | 0.19 | 81% |

The percent tumor growth inhibition (% TGI) is calculated by:

$$\% \, TGI = 1 - \frac{(\text{final size} - \text{starting size})_{treated}}{(\text{final size} - \text{starting size})_{control}} \times 100$$

Example 4

In vivo Determination of Inhibition of Tumor Growth

Figure 7:
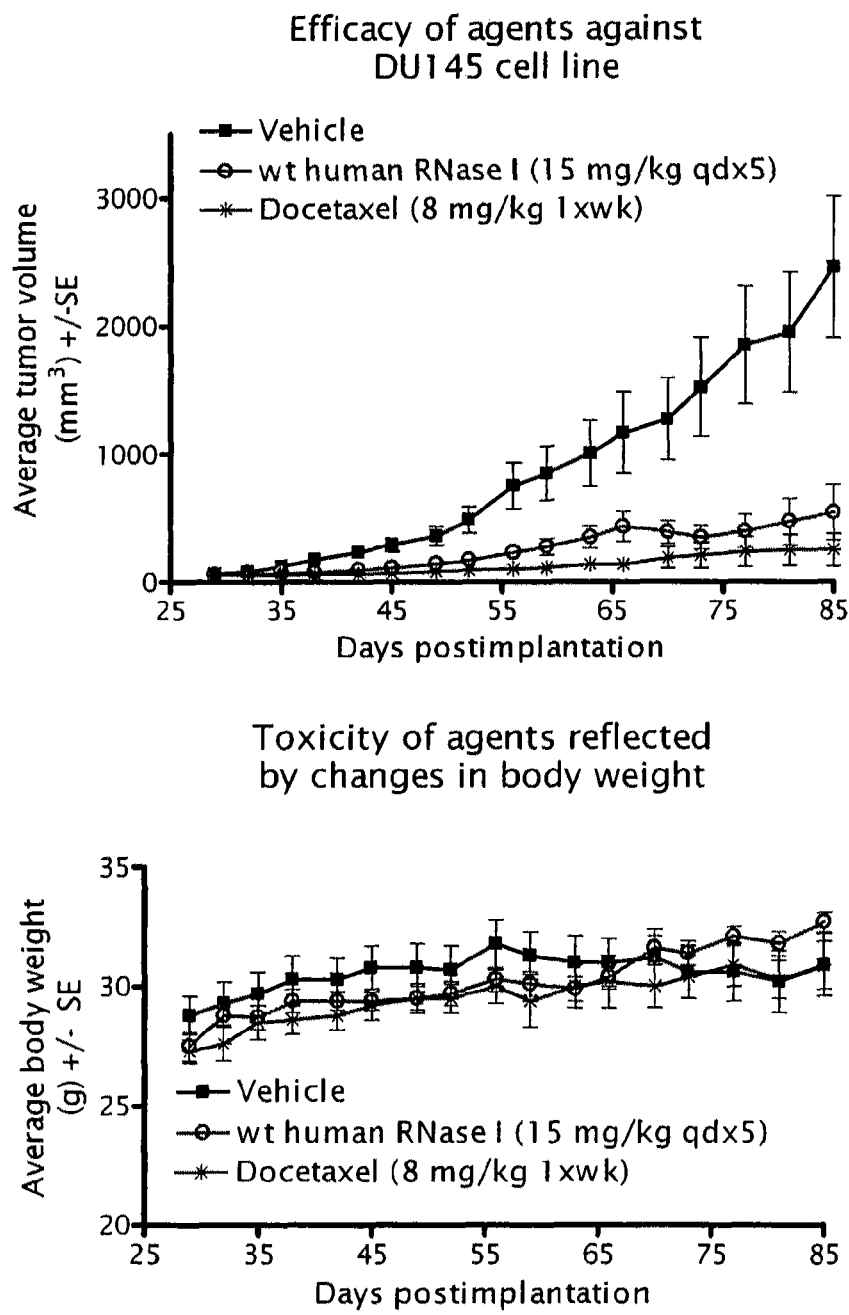
FIG. 7 shows in vivo activity of RNases in some embodiments of the present invention.

This xenograft model was set up as in the previous example except that a human prostate cancer cell line (DU145) was used. The efficacy of wild type human RNase 1 is shown relative to docetaxel. The RNase 1 was administered at 75 mg per kg of body weight of the animal (75 mg/kg 1×wk), while the docetaxel was used at 8 mg/kg once a week. The value of n represents the number of animals in the specific treatment arm of the experiment. Results are shown in FIG. 7 and Table 8.

TABLE 8

|  | Starting volume | Final volume | (Final − start) | (Final − start)/ Control | % TGI |
|---|---|---|---|---|---|
| Vehicle | 64 | 2452 | 2388 | 1 | 0 |
| wt human RNase 1 | 61 | 539 | 478 | 0.20 | 80 |
| Docetaxel | 60 | 249 | 180 | 0.08 | 92 |

Clinical Chemistry and Complete Blood Count Plus Platelets

Figure 8:
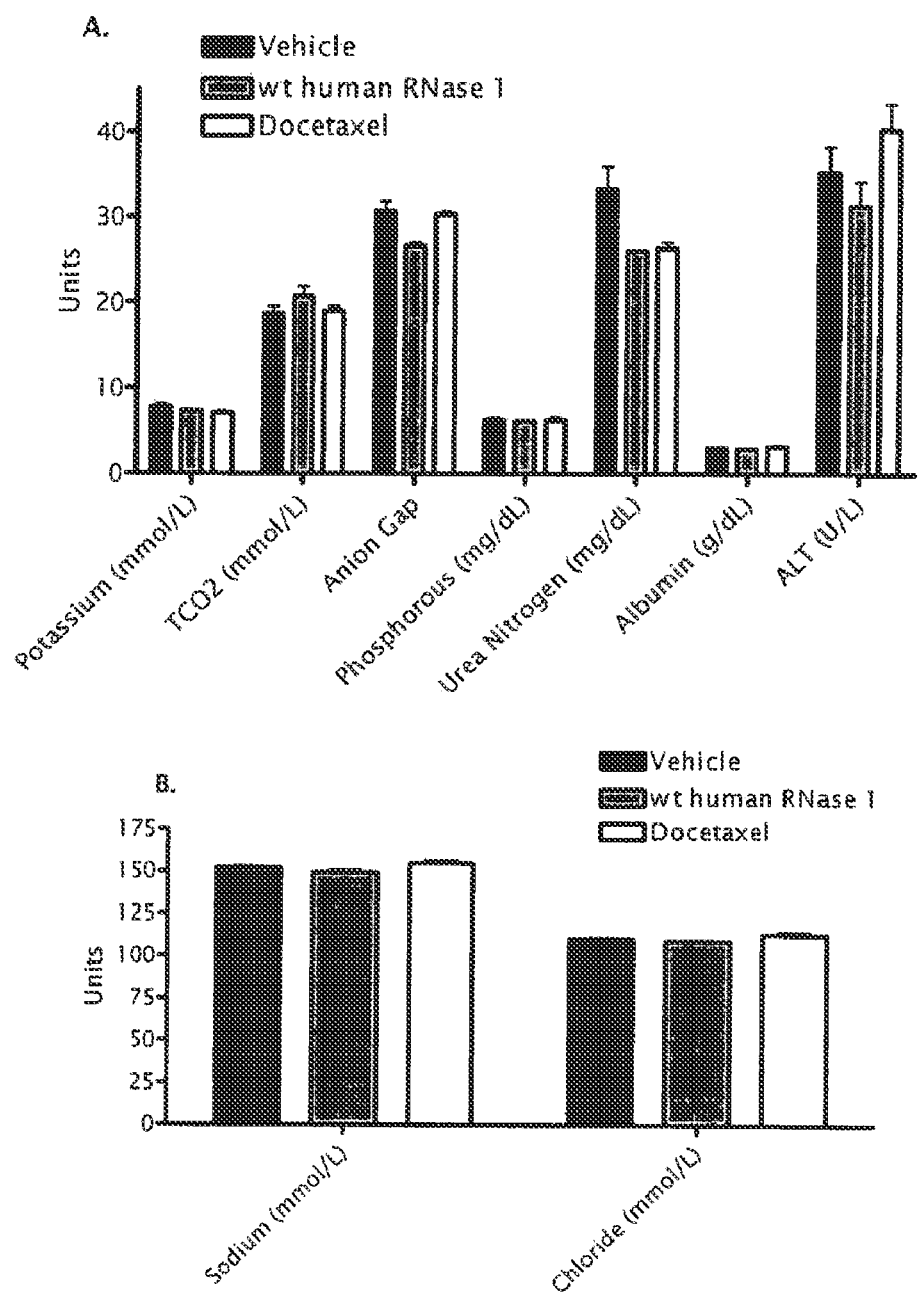
FIG. 8 shows toxicity testing data in some embodiments of the present invention.
Figure 8:
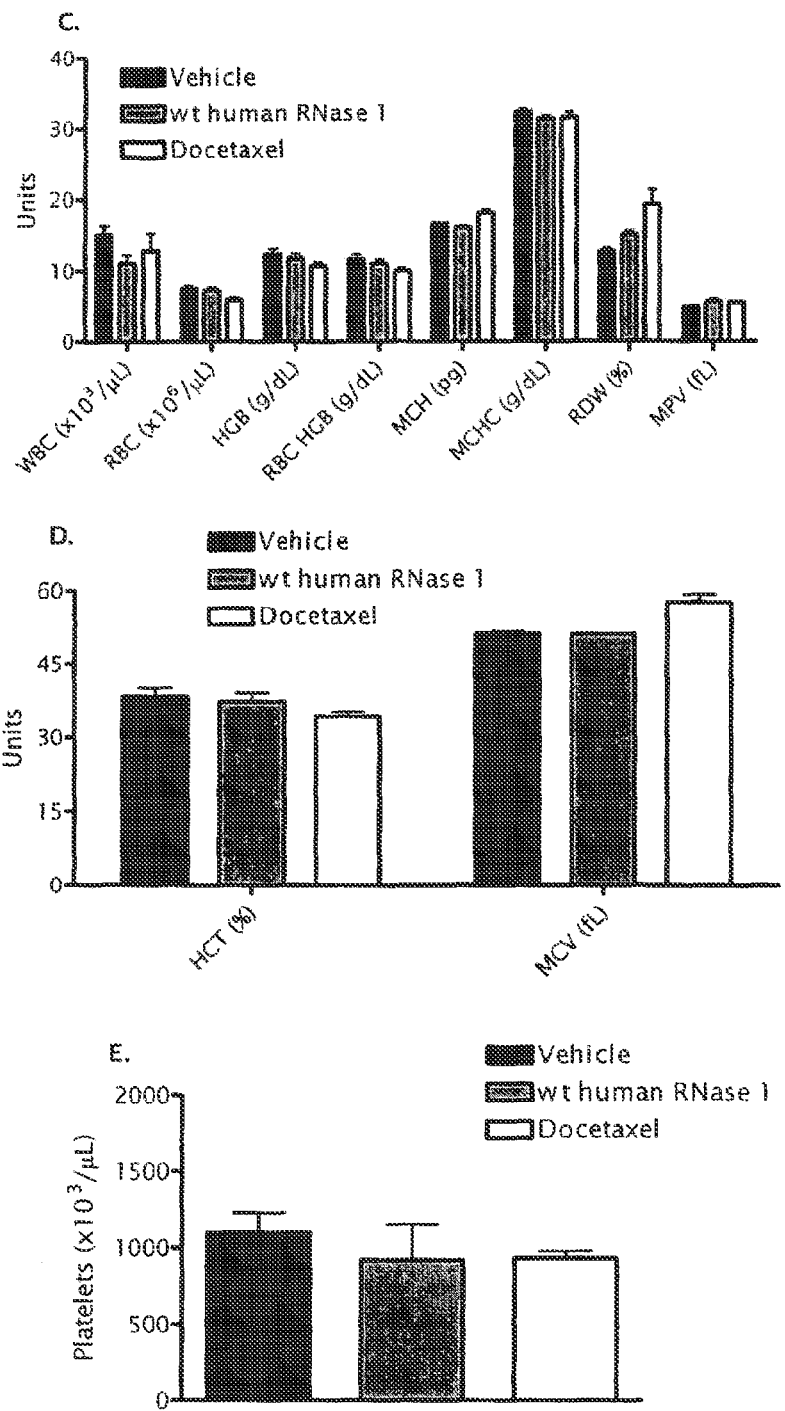

Clinical chemistry and a complete blood count (CBC) plus platelets were performed on whole blood and serum samples collected from the mice 24 hours after the last treatment of the prostate xenograft model above. In all tests, the results for wild type human RNase 1 and docetaxel were determined not to be significantly different from the vehicle treated animals (Mann-Whitney U test). Creatinine was also tested and found not to differ. The levels of the liver enzymes, gamma glutamyl transferase (GGT) and alanine transaminase (ALT) in all treatment groups were similar (GGT data not shown.). Results are shown in FIG. 8. The values were determined for the various treatment groups of the prostate (DU145) xenograft study for clinical chemistry (A., B.), complete blood count (C., D.), and platelets (F.). Abbreviations: $TCO_2$, amount of bicarbonate ion ($HCO_3^-$); Anion Gap, [Na+K]—[Cl+$HCO_3$]; ALT, alanine aminotransferase; WBC, white blood count; RBC, red blood count; HGB, hemoglobin; RBC HGB, (CHCM×RBC×MCV)/1000); MCH, mean corpuscular hemoglobin; MCHC, mean corpuscular hemoglobin concentration; RDW, red cell distribution width; MPV, mean platelet volume; HCT, hematocrit; MCV, mean corpuscular volume.

Example 5

In vivo Determination of Inhibition of Tumor Growth

Figure 9:
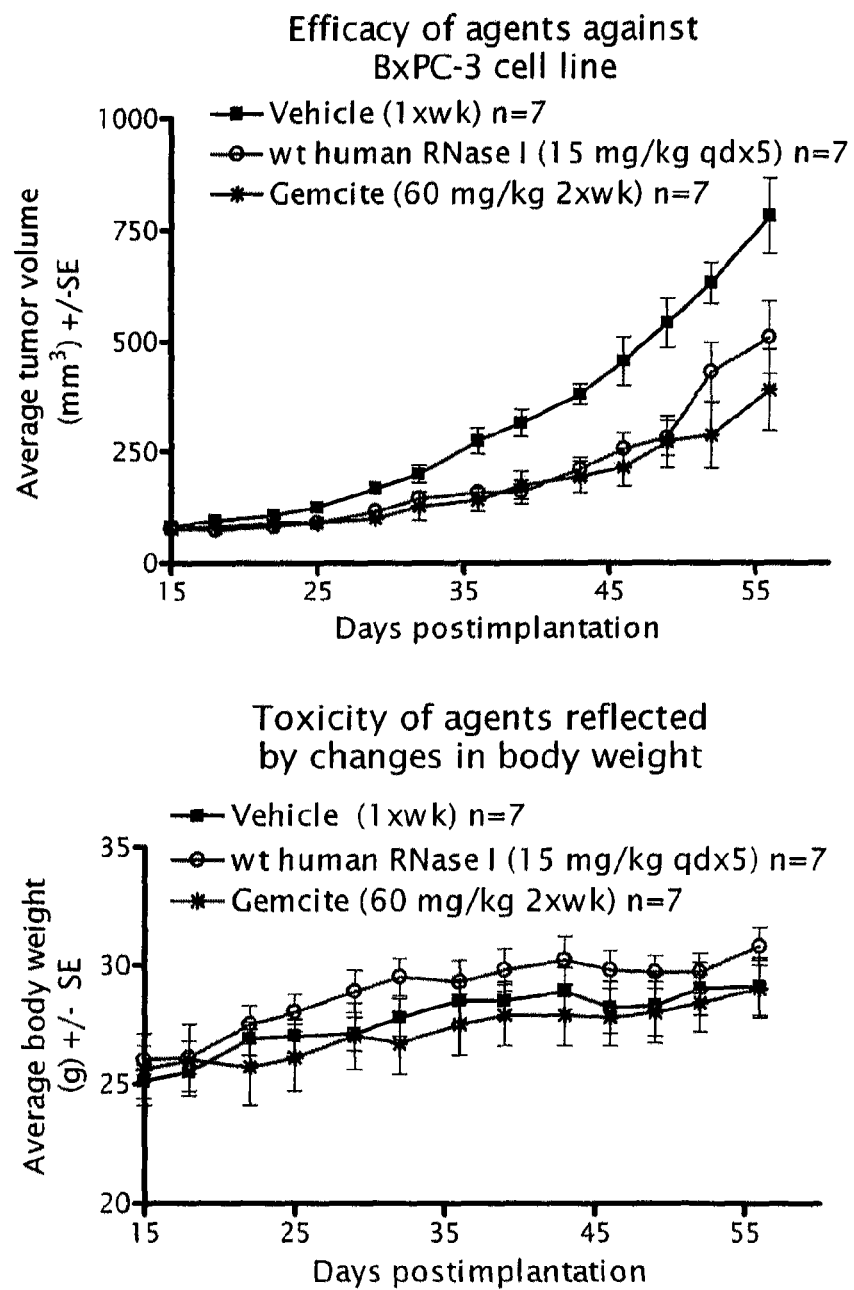
FIG. 9 shows in vivo activity of RNases in some embodiments of the present invention.

The xenograft model of this example was set up as in the previous example except that a human pancreatic cancer cell line (BxPC-3) was used. The efficacy of wild type human RNase 1 is shown relative to gemcite. The RNase 1 was administered at 15 mg per kg of body weight of the animal five times per week (15 mg/kg qd×5), while the gemcite was used at 60 mg/kg twice a week. The value of n represents the number of animals in the specific treatment arm of the experiment. Results are shown in FIG. 9 and Table 9.

TABLE 9

|  | Starting volume | Final volume | (Final − start) | (Final − start)/ Control | % TGI |
|---|---|---|---|---|---|
| Vehicle | 81 | 1158 | 1077 | 1 | 0 |
| wt human RNase 1 | 77 | 899 | 822 | 0.76 | 24 |
| Gemcite | 78 | 505 | 427 | 0.40 | 60 |

Example 6

In vivo Determination of Inhibition of Tumor Growth

Figure 10:
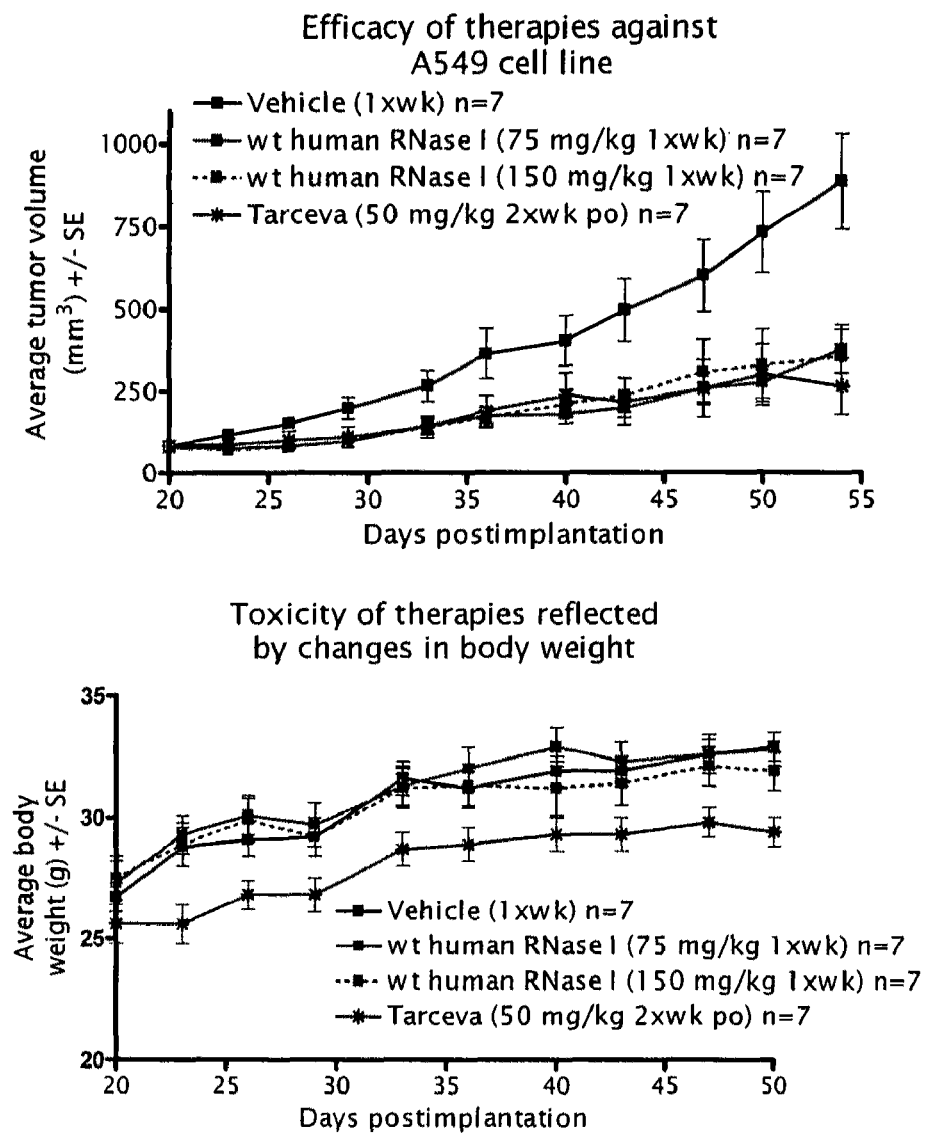
FIG. 10 shows in vivo activity of RNases in some embodiments of the present invention.

The xenograft model of this example was set up with the human non-small cell lung cancer cell line (A549) as in the previous examples. The efficacy of wild type human RNase 1 is shown relative to tarceva. The RNase 1 was administered at 75 mg per kg of body weight of the animal (75 mg/kg 1×wk) or 150 mg/kg 1×wk. Tarceva was given orally with doses of 50 mg/kg twice a week. The value of n represents the number of animals in the specific treatment arm of the experiment. Results are shown in FIG. 10 and Table 10.

TABLE 10

|  | Starting volume | Final volume | (Final − start) | (Final − start)/ Control | % TGI |
|---|---|---|---|---|---|
| Vehicle | 83 | 886 | 803 | 1 | 0 |
| wt human RNase 1 (75 mg) | 78 | 378 | 300 | 0.37 | 63 |
| wt human RNase 1 (150 mg) | 79 | 355 | 276 | 0.34 | 66 |
| Tarceva | 84 | 265 | 181 | 0.23 | 77 |

Example 7

In vivo Determination of Inhibition of Tumor Growth

Figure 11:
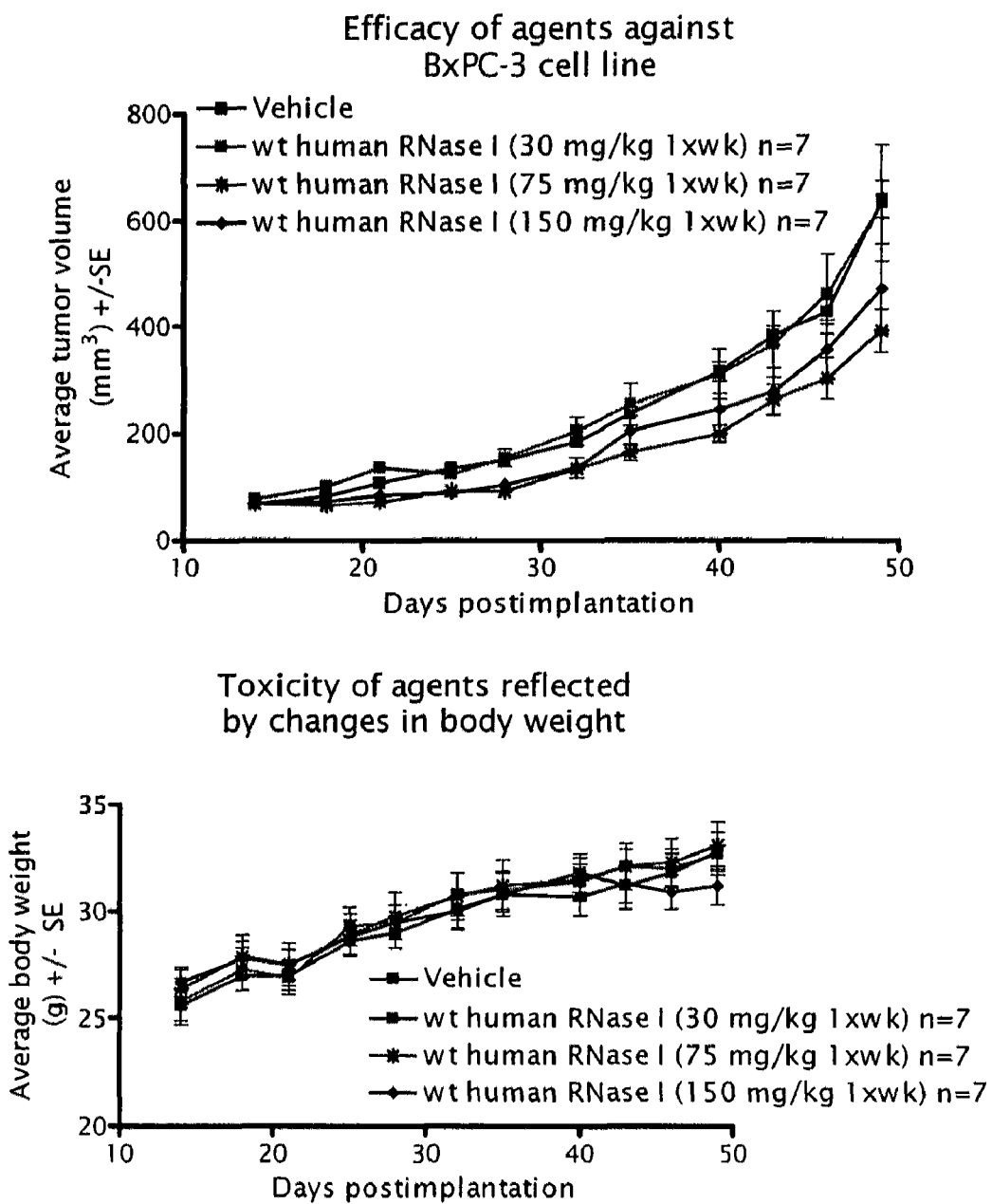
FIG. 11 shows in vivo activity of RNases in some embodiments of the present invention.

The xenograft model of this example was set up as in the previous example except that a human pancreatic cancer cell line (BxPC-3) was used. The efficacy of wild type human RNase 1 is shown. The RNase 1 was administered at three different doses: (1) 30 mg per kg of body weight of the animal once per week (30 mg/kg 1×wk), (2) 75 mg/kg 1×wk, or (3) 150 mg/kg 1×wk. The value of n represents the number of animals in the specific treatment arm of the experiment. Results are shown in FIG. 11 and Table 11.

TABLE 11

|  | Starting volume | Final volume | (Final − start) | (Final − start)/ Control | % TGI |
|---|---|---|---|---|---|
| Vehicle | 70 | 639 | 569 | 1 | 0 |
| wt human RNase 1 (30 mg) | 78 | 632 | 554 | 0.97 | 3 |
| wt human RNase 1 (75 mg) | 69 | 392 | 323 | 0.57 | 43 |
| wt human RNase 1 (150 mg) | 69 | 471 | 402 | 0.71 | 29 |

Example 8

In vivo Determination of Inhibition of Tumor Growth

Figure 12:
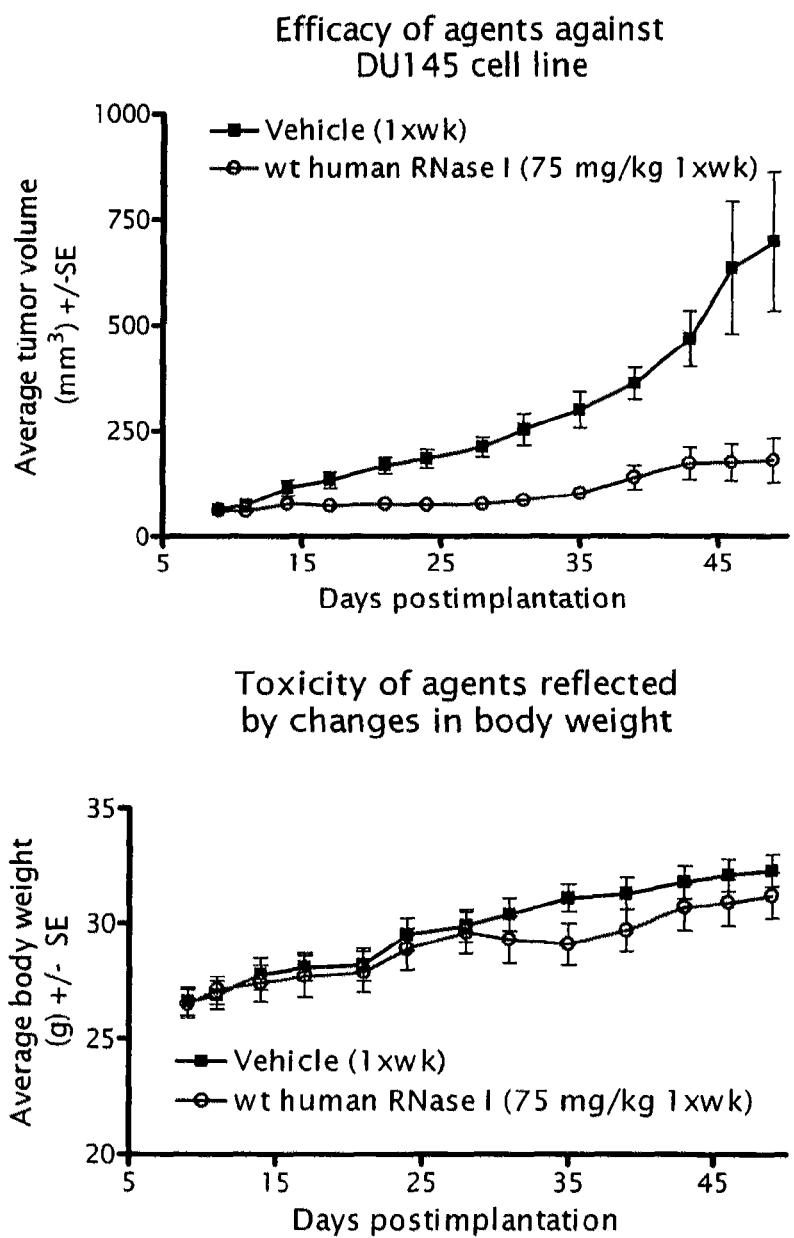
FIG. 12 shows in vivo activity of RNases in some embodiments of the present invention.

The xenograft model of this example was set up as in the previous example except that a human prostate cancer cell line (DU145) was used. The efficacy of wild type human RNase 1 is shown. The RNase 1 was administered at 75 mg per kg of body weight of the animal once per week (75 mg/kg 1×wk). The value of n represents the number of animals in the specific treatment arm of the experiment. Results are shown in FIG. 12 and Table 12.

TABLE 12

|  | Starting volume | Final volume | (Final − start) | (Final − start)/ Control | % TGI |
|---|---|---|---|---|---|
| Vehicle | 63 | 2732 | 2669 | 1 | 0 |
| wt human RNase 1 (75 mg) | 62 | 669 | 607 | 0.23 | 77% |

Example 9

In vivo Determination of Inhibition of Tumor Growth

Figure 13:
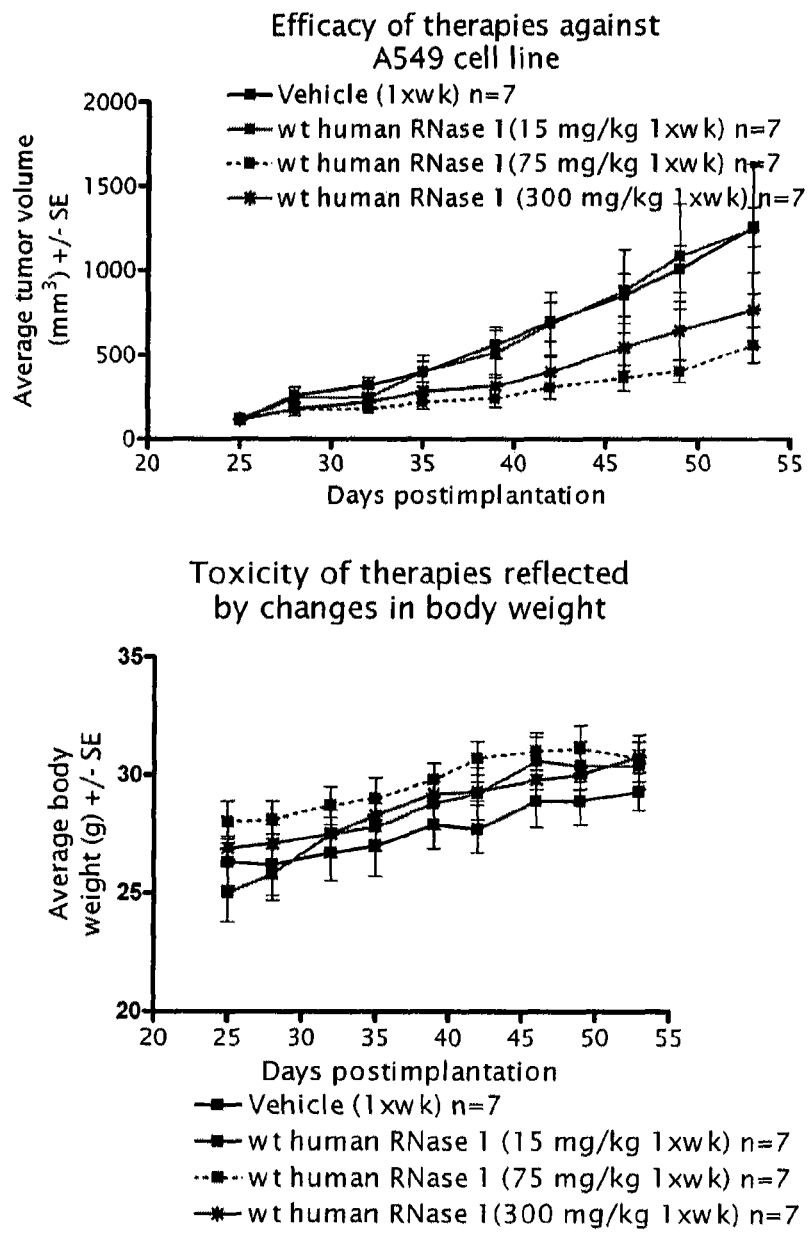
FIG. 13 shows in vivo activity of RNases in some embodiments of the present invention.

The xenograft model of this example was set up as in the previous example. The efficacy of wild type human RNase 1 is shown. The RNase 1 was administered at three different doses: (1) 15 mg per kg of body weight of the animal once per week (15 mg/kg 1×wk), (2) 75 mg/kg 1×wk, or (3) 300 mg/kg 1×wk. The value of n represents the number of animals in the specific treatment arm of the experiment. Results are shown in FIG. 13 and Table 13.

TABLE 13

|  | Starting volume | Final volume | (Final − start) | (Final − start)/ Control | % TGI |
|---|---|---|---|---|---|
| Vehicle | 117 | 1256 | 1139 | 1 | 0 |
| wt human RNase 1 (15 mg) | 110 | 1246 | 1136 | 1 | 0 |
| wt human RNase 1 (75 mg) | 114 | 559 | 445 | 0.39 | 61% |
| wt human RNase 1 (300 mg) | 114 | 766 | 652 | 0.57 | 43% |

Example 10

In vivo Determination of Inhibition of Tumor Growth

Figure 14:
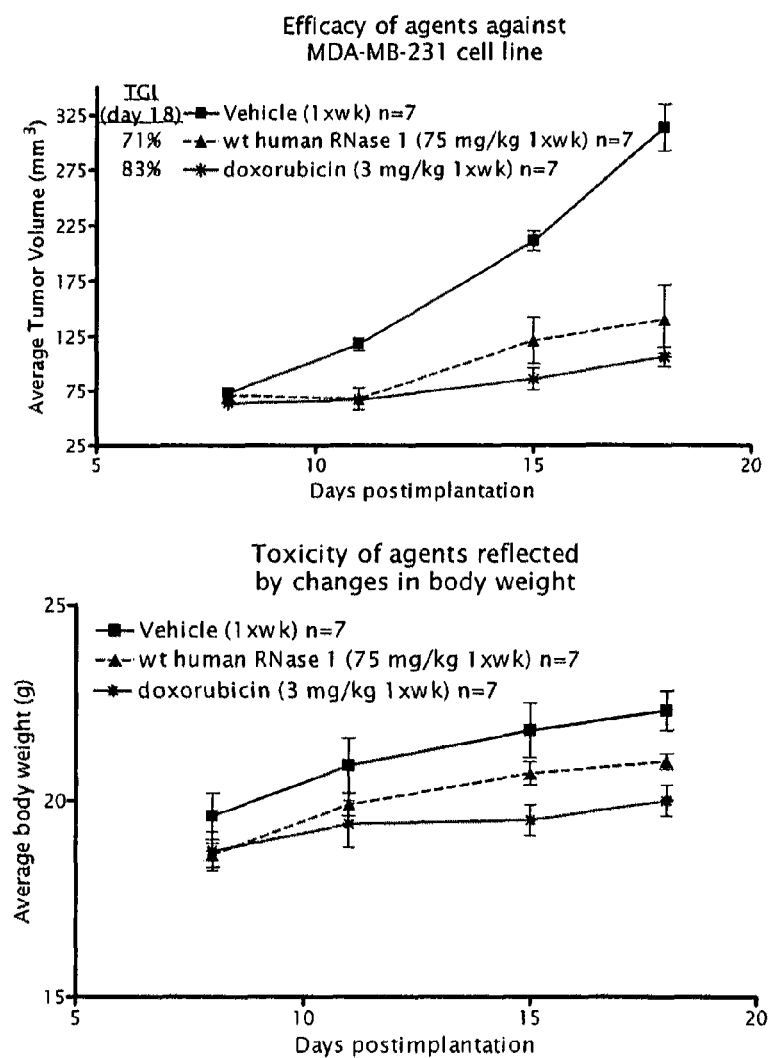
FIG. 14 shows in vivo activity of RNases in some embodiments of the present invention.

The xenograft model of this example was set up as in the previous example except that a human breast cancer cell line (MDA-MB-231) and female mice were used. The efficacy of wild type human RNase 1 is shown relative to doxorubicin. The RNase 1 was administered at 75 mg per kg of body weight of the animal once per week (75 mg/kg 1×wk), while the doxorubicin was given at 3 mg/kg once per week. The value of n represents the number of animals in the specific treatment arm of the experiment. Results are shown in FIG. 14 and Table 14.

TABLE 14

|  | Starting volume | Final volume | (Final − start) | (Final − start)/ Control | % TGI |
|---|---|---|---|---|---|
| Vehicle | 73 | 211 | 138 | 1 | 0 |
| wt human RNase 1 (75 mg) | 71 | 121 | 50 | 0.36 | 64% |
| doxorubicin (3 mg) | 64 | 86 | 22 | 0.16 | 84% |

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A method for inhibiting tumor growth in a human subject having a cancer selected from the group consisting of breast, lung, prostate, pancreatic, skin, colon, ovarian, head-neck, liver, bladder, cervical, testicular, stomach, thyroid, esophageal, or renal cancer, the method comprising parenterally administering a pharmaceutical composition comprising recombinantly produced and purified wild type human ribonuclease 1 (wthRNase 1) to said subject in an amount effective for inhibiting the tumor growth of the cancer.

2. The method of claim 1, wherein said tumor comprises a stem cell.

3. The method of claim 1, further comprising treating the subject with a therapeutic dose of radiation.

4. The method of claim 1, wherein administering said pharmaceutical composition to said subject comprises administering at a dose of 15 to 300 mg/kg body weight with respect to said subject.

5. The method of claim 1, wherein said administering comprises administering at a frequency of between 1 and 5 times per week.

6. The method of claim 1, wherein said wthRNase 1 is parenterally administered in a form wherein the wthRNase 1 is conjugated to a drug.

7. The method of claim 1, wherein the administering of said pharmaceutical composition comprises administering to the subject a dose of 1 to 500 mg/kg body weight with respect to said subject.

8. The method of claim 7, wherein said administering comprises administering at a frequency of between 1 and 14 times per week.

9. A method for inhibiting tumor growth in a human subject having a cancer selected from the group consisting of breast, lung, prostate, and pancreatic cancer, the method comprising the step of parenterally administering 15 to 300 mg/kg body weight of a pharmaceutical composition comprising an effective amount of recombinantly produced and purified wild type human ribonuclease 1 (wthRNase 1) to said subject.

* * * * *